(12) United States Patent
Kaku et al.

(10) Patent No.: US 10,974,619 B2
(45) Date of Patent: Apr. 13, 2021

(54) VEHICLE SEAT AND PASSENGER SELECTION SYSTEM

(71) Applicant: TS TECH CO., LTD., Saitama (JP)

(72) Inventors: Hiroyuki Kaku, Tochigi (JP); Hiroyuki Numajiri, Tochigi (JP); Hitomi Kobayashi, Tochigi (JP); Takako Miyoshi, Tochigi (JP); Satoshi Fujita, Tochigi (JP); Katsuhiko Abe, Tochigi (JP); Hajime Yoshida, Tochigi (JP); Takahiro Mitsui, Tochigi (JP); Tomoyuki Kurimoto, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 138 days.

(21) Appl. No.: 15/935,416

(22) Filed: Mar. 26, 2018

(65) Prior Publication Data

US 2018/0281621 A1 Oct. 4, 2018

(30) Foreign Application Priority Data

| Mar. 28, 2017 | (JP) | JP2017-063932 |
| Mar. 28, 2017 | (JP) | JP2017-063934 |
| Mar. 28, 2017 | (JP) | JP2017-063935 |

(51) Int. Cl.
*B60N 2/00* (2006.01)
*B60N 2/015* (2006.01)
(Continued)

(52) U.S. Cl.
CPC ............ *B60N 2/002* (2013.01); *A61B 5/0022* (2013.01); *A61B 5/18* (2013.01); *A61B 5/6893* (2013.01);
(Continued)

(58) Field of Classification Search
CPC . B60N 2/68; B60N 2/682; B60N 2/90; B60N 2/919; B60N 2002/924
(Continued)

(56) References Cited

U.S. PATENT DOCUMENTS 5,637,010 A * 6/1997 Jost ................... H01R 13/6277
439/352
5,823,812 A * 10/1998 Bhargava ........... H01R 13/6278
439/345
(Continued)

FOREIGN PATENT DOCUMENTS

| DE | 19743313 C1 * 12/1998 ........... B60R 16/027 |
| JP | 2003299549 10/2003 |

(Continued)

OTHER PUBLICATIONS

Japan Office Action for JP2017063932 dated Feb. 16, 2021, 8 pages.
(Continued)

*Primary Examiner* — Hilary L Gutman
(74) *Attorney, Agent, or Firm* — Dority & Manning, P.A.

(57) ABSTRACT

A vehicle seat comprises a frame member provided on a floor of a vehicle, a seat part such as a seat cushion detachably attached to the frame member, a mechanical connector device provided on the frame member and the seat part for detachably attaching the seat part to the frame member; and an electric connector device provided on the frame member and the seat part for electrically connecting an electric component provided on the seat part to an electric component provided on the frame member.

5 Claims, 18 Drawing Sheets

(51) Int. Cl.
 *B60N 2/90*  (2018.01)
 *A61B 5/00*  (2006.01)
 *A61B 5/18*  (2006.01)
 *B60N 2/70*  (2006.01)
 *B60N 2/427*  (2006.01)
 *B60N 2/68*  (2006.01)
 *B60N 2/882*  (2018.01)
 *B60N 2/02*  (2006.01)

(52) U.S. Cl.
 CPC ........... *B60N 2/015* (2013.01); *B60N 2/4279* (2013.01); *B60N 2/42745* (2013.01); *B60N 2/42754* (2013.01); *B60N 2/68* (2013.01); *B60N 2/682* (2013.01); *B60N 2/686* (2013.01); *B60N 2/70* (2013.01); *B60N 2/7005* (2013.01); *B60N 2/882* (2018.02); *B60N 2/90* (2018.02); *B60N 2/914* (2018.02); *A61B 2503/22* (2013.01); *A61B 2562/227* (2013.01); *B60N 2002/0264* (2013.01)

(58) Field of Classification Search
 USPC .......................................... 439/34; 296/65.03
 See application file for complete search history.

(56) References Cited

U.S. PATENT DOCUMENTS

| | | | | |
|---|---|---|---|---|
| 6,050,835 | A * | 4/2000 | Henrion | B60N 2/01516 439/247 |
| 6,250,703 | B1 * | 6/2001 | Cisler | B60N 2/01583 296/65.03 |
| 6,257,641 | B1 * | 7/2001 | Fritz | B60N 2/01583 296/65.03 |
| 6,279,981 | B1 * | 8/2001 | Mesnage | B60N 2/002 296/65.03 |
| 6,663,157 | B1 * | 12/2003 | Hofmann | B60N 2/01516 248/503.1 |
| 6,676,129 | B2 * | 1/2004 | Wilson | B60J 3/0217 296/97.12 |
| 7,008,255 | B1 * | 3/2006 | Wang | H01R 13/506 439/357 |
| 7,942,477 | B1 | 5/2011 | Toba et al. | |
| 9,950,633 | B2 * | 4/2018 | Lee | G06Q 50/06 |
| 2002/0105203 | A1 * | 8/2002 | Hansen | B60N 2/01583 296/65.03 |
| 2007/0132265 | A1 * | 6/2007 | Tsukamoto | B60N 2/0155 296/65.03 |
| 2007/0246285 | A1 | 10/2007 | Browne et al. | |
| 2009/0267376 | A1 * | 10/2009 | McDermott | B60N 2/01591 296/65.03 |
| 2013/0158895 | A1 | 6/2013 | Bessho et al. | |
| 2013/0224969 | A1 * | 8/2013 | Sasaki | H01R 31/06 439/34 |
| 2015/0280342 | A1 * | 10/2015 | Kato | H01R 13/115 439/34 |
| 2015/0291072 | A1 | 10/2015 | Ito | |

FOREIGN PATENT DOCUMENTS

| | | |
|---|---|---|
| JP | 2004186039 | 7/2004 |
| JP | 2006054118 | 2/2006 |
| JP | 2009119230 | 6/2009 |
| JP | 2009208495 | 9/2009 |
| JP | 2010017345 | 1/2010 |
| JP | 2010253182 | 11/2010 |
| JP | 2013129250 | 7/2013 |
| JP | 2014215670 | 11/2014 |

OTHER PUBLICATIONS

Japan Office Action for JP2017063934 dated Feb. 16, 2021, 10 pages.

* cited by examiner

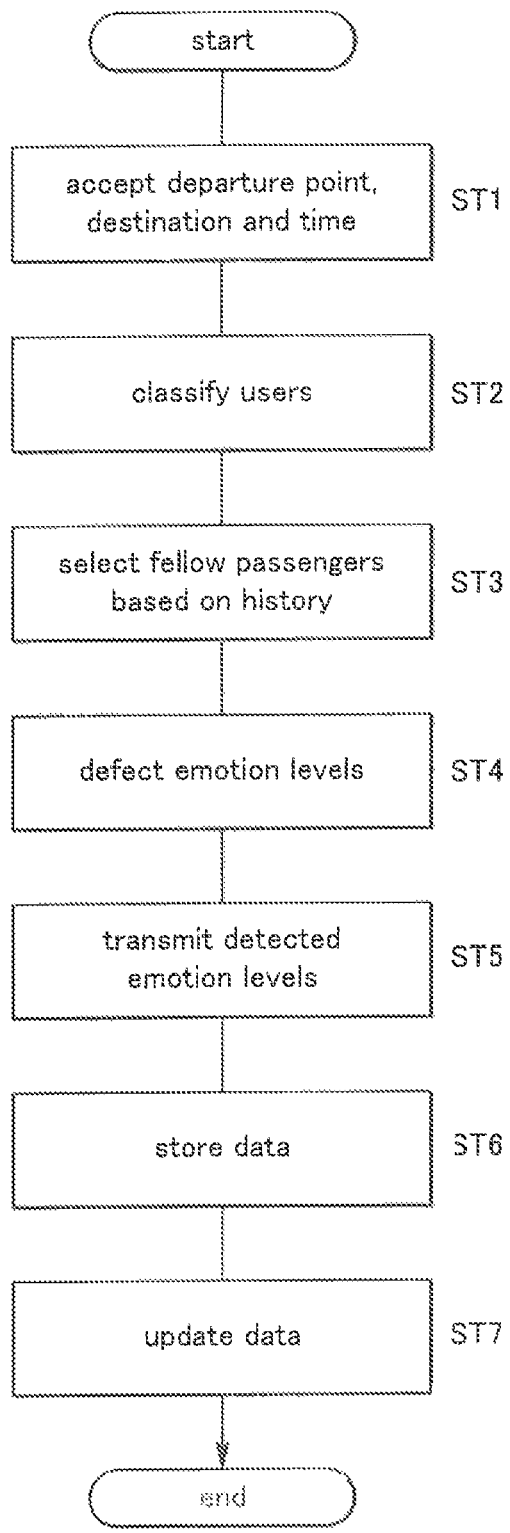

VEHICLE SEAT AND PASSENGER SELECTION SYSTEM

TECHNICAL FIELD

The present invention relates to a vehicle seat, and a passenger selection system for use in carpooling or any other car sharing system.

BACKGROUND ART

A vehicle seat disclosed in JP2010-253182A is provided with a seat cushion and a seat back, and each of the seat cushion and the seat back is formed by a central part, and a pair of side parts which are interchangeable. By selecting the side parts of the seat cushion and/or the seat back, the vehicle seat can be adapted to the need of a user. Also, if the side parts are worn or damaged, they can be replaced with new ones.

However, according to this prior art, replacing and installing side parts require some work. Also, if the seat contains any electric device, replacing or installing side parts requires rewiring of the electric device. This also complicates the replacing or installing work.

Therefore, there is a need for a novel vehicle seat that can be adapted to the need of a user in a simpler manner.

In a vehicle seat disclosed in JP2009-19230A, the shape and the softness of a support surface of the vehicle seat can be adjusted. A plurality of air bladders are incorporated in the seat cushion and the seat back and pressure sensors are arranged over a support surface of the vehicle seat. The air bladders are connected to an air pump, and a control device controls the air pressure supplied to each air bladder by supplying an appropriate pressure from the pump to each air bladder according to the output signals of the pressure sensors.

According to this prior art, in order to adjust the distribution of softness finely over the support surface, it is necessary to arrange a large number of small air bladders over the entire area of the support surface. Therefore, piping for the air bladders becomes highly complex, and supplying air pressure to each bladder requires a highly complex control arrangement.

Therefore, there is a need for a novel vehicle seat that can adjust the distribution of the softness of a support surface thereof in a simpler manner.

For environmental considerations, various systems of car pooling or ride sharing have been proposed. In a car sharing system proposed in JP2014-215670A, fellow passengers are selected from those who trust one another. Trustworthiness is evaluated on the basis of personal relationships which may be manifested in the listing of addresses in a personal terminal device of each user. If a subject user's address is listed in the personal terminal of a first user, the subject user and the first user may be considered to be trustworthy of each other by a first degree. If a subject user's address is listed in the personal terminal of a first user, and the first user's address is listed in a second user, the subject user and the second user may be considered to be trustworthy to each other by a second degree.

This system preferentially selects users who are relatively familiar to each other, but this does not ensure that the two users are on a friendly term or able to sit together comfortably.

Therefore, there is a need for a passenger selection system that can select fellow passengers in a ride share system so as to optimize of the comfort of each passenger.

SUMMARY OF THE INVENTION

In view of such problems of the prior art, a primary object of the present invention is to provide a vehicle seat that is provided with interchangeable seat parts that can be readily changed while allowing electric connection to be achieved at the same time in an effortless manner.

A second object of the present invention is to provide a vehicle seat that can adjust the stiffness of a pressure receiving surface thereof for the maximum comfort of the seat occupant.

A third object of the present invention is to provide a passenger selection system for a ride share that can optimize the comfort of the user by selecting fellow passengers by using data obtained from a biometric sensor incorporated in the seat.

To accomplish at least some of such objects, a first aspect of the present invention provides a vehicle seat, comprising: a frame member provided on a floor of a vehicle; a seat part detachably attached to the frame member; a mechanical connector device provided on the frame member and the seat part for detachably attaching the seat part to the frame member, and an electric connector device provided on the frame member and the seat part for electrically connecting an electric component provided on the seat part to an electric component provided on the frame member.

Thereby, the seat part, such as a seat cushion, a seat back and a head rest, can be readily attached to and removed from the seat frame both mechanically and electrically in a highly simple and effortless manner so that the seat can be adjusted to the need of the user in a convenient manner. The electric connection as used herein should not be limited to literal electric connection, but should be understood to mean any mode of arrangement for enabling transmission of power and/or signals in optical, acoustic or any other form.

Preferably, the electric connector device is integrally incorporated in the mechanical connector device.

Thereby, the attachment and detachment of the seat part to and from the frame member are maximally simplified.

According to a preferred embodiment of the present invention, the mechanical connector device is provided with a first tube provided on the seat part, and a second tube provided on the frame member and configured to be fitted into or onto the first tube, and the electric connector device includes a first part received in the first tube and a second part received in the second tube.

By fitting one of the tubes into or onto the other, a highly mechanical connection can be achieved by using a highly simple structure. A suitable latch mechanism may be used to further enhance the stability of the mechanical connection. By placing the electric connector device in these tubes, the electric connector device can be protected from damages from external forces and foreign matters.

In a particularly preferred embodiment of the present invention, the first part of the electric connector device is provided with an identifier carrying prescribed information, and the second part of the electric connector device is provided with a recognition device configured to read information carried by the identifier.

Thereby, the attributes of each seat part can be identified as soon as the seat part is joined to the frame member so that the control device of the vehicle is enabled to control the seat part or any devices associated therewith in a proper manner without requiring any human intervention.

In a certain embodiment of the present invention, the seat part includes at least a first seat part segment which is detachably attached to the frame member via the mechanical connector device and the electric connector device, and a second seat part segment which is detachably attached to the first seat part segment via a segment mechanical connector device provided on the first seat part segment and the second seat part segment.

Thereby, the seat can be adapted to the user in a finely adjusted manner. Also, the seat can be repaired by replacing a damaged part thereof, instead of replaying the entire seat.

According to another aspect of the present invention, the electric component provided on the seat part includes a plurality of pressure sensors arranged over a pressure supporting surface of the seat part and each configured to detect a pressure applied thereto, and a plurality of actuators arranged over the pressure supporting surface of the seat part and each configured to change a localized stiffness of the pressure supporting surface of the seat part, and the electric component provided on the frame member includes a control device or a wiring leading to a control device, the control device being configured to control operation of the actuators according to output signals from the pressure sensors.

Thereby, the level of stiffness of various parts of the pressure receiving surface can be adjusted so as to optimize the comfort and support of the seat occupant.

In a particularly preferred embodiment of the present invention, the seat part includes a sub frame configured to be detachably attached to the frame member, a pad supported by the sub frame and a skin member covering a surface of the pad, and the actuators are interposed between the skin member and the pad.

Thereby, the actuators are protected from damages, and the change in stiffness caused by each actuator can be transmitted favorably to the seat occupant.

Preferably, the pressure sensors are incorporated in a pressure sensor sheet interposed between skin member and the pad.

Thereby, the pressure sensors can detect the pressure values in an accurate manner, and can be installed in a highly simple manner. The pressure sensors may be incorporated in the skin member to further enhance these advantages. The actuators may also be incorporated in a soft actuator sheet interposed between the skin member and the pad.

Preferably, the soft actuator sheet comprises linear actuators extending in a lateral direction of the seat part and arranged in a longitudinal direction of the seat part, and each configured to change a tension thereof according to an input signal supplied thereto.

Thereby, the pressure actuators can be prepared and installed in a simple manner, and the stiffness variations in the longitudinal direction can be produced in an effective and simple manner.

The soft actuator sheet may further comprise linear actuators extending in the longitudinal direction of the seat part and arranged in the lateral direction of the seat part, and each configured to change a tension thereof according to an input signal supplied thereto.

Thereby, the stiffness variations in the pressure support surface in the longitudinal direction can be produced in an effective and simple manner.

To further simplify the arrangement, the pressure sensors may comprise linear pressure sensors incorporated in the soft actuator sheet. Thereby, the structure for the pressure sensors can be simplified.

Preferably, the pad and/or the sub frame is provided with a recess configured to receive wiring leading from the electric component provided on the seat part to the electric connector device provided on the seat part.

Thereby, the wiring can be passed through the seat part without impairing the seating comfort of the seat part.

A third aspect of the present invention provides a passenger selection system including the vehicle seat according to the first aspect of the present invention, the system comprising: a detection unit including a biometric sensor provided on the seat part and configured to detect an index pertaining to emotion of each user seated in the seat to a fellow passenger sharing a ride with the user; a storage unit for storing a history of the indices of the user in relation to the fellow passengers detected during rides that were shared in the past; and a computation unit for selecting a fellow passenger for a next ride to be shared by the user according to the history stored in the storage unit.

Thereby, the users are enabled to share vehicles with maximum comfort in a subtle way. Since the biometric sensor is provided on the seat part, the users are not required to wear any device on their persons, and the comfort and convenience of the users can be maximized.

Preferably, the storage unit and the computation unit are provided in a data center provided separately from the vehicle. Thereby, the data can be processed and controlled centrally so that the risk of leaking personal data can be minimized.

The vehicle may be provided with a wireless transmitter for sending detection results of the biometric sensor to the data center. Thereby, the data can be transmitted to the data center promptly.

Preferably, the computation unit is configured to analyze the history of the indices stored in the storage unit, and select a fellow passenger for a next ride to be shared by the user according to an analysis result.

Thereby, the process of selecting the fellow passengers can be performed in an automated manner. In this conjunction, the computation unit may be configured to select a fellow passenger for the user from those to whom the user registered higher levels of emotion than others as recorded in the history. Alternatively, the computation unit may be configured to select a fellow passenger for the user by eliminating those to whom the user registered lower levels of emotion than others as recorded in the history.

According to another aspect of the present invention, the computation unit is configured to group the users of the system into a plurality of groups such that the users in each group register high emotional level toward each other, and select a fellow passenger for each user from the group to which the particular user belongs.

This arrangement also allows each user to share rides with fellow passengers the user is most comfortable to share a ride with.

BRIEF DESCRIPTION OF THE DRAWING(S)

FIG. 18 is a flowchart showing a control action of the passenger selection system.

DESCRIPTION OF THE PREFERRED EMBODIMENT(S)

Preferred embodiments of the present invention are described in the following with reference to the appended drawings. The directions as used in the following disclosure are based on the view point of the vehicle occupant in the seat.

Figure 1:
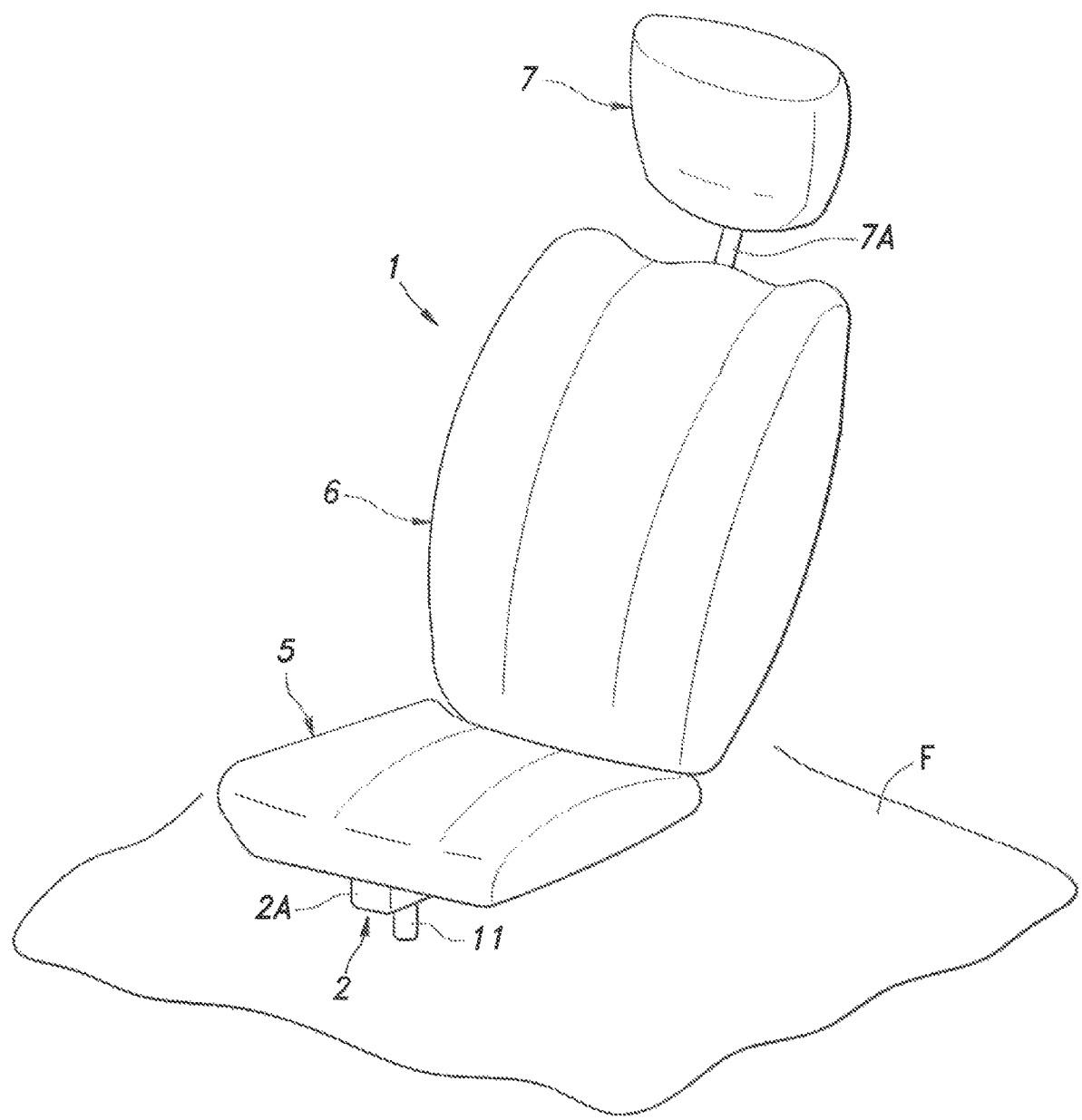
FIG. 1 is a perspective view of a vehicle seat according to a first embodiment of the present invention.
Figure 2:
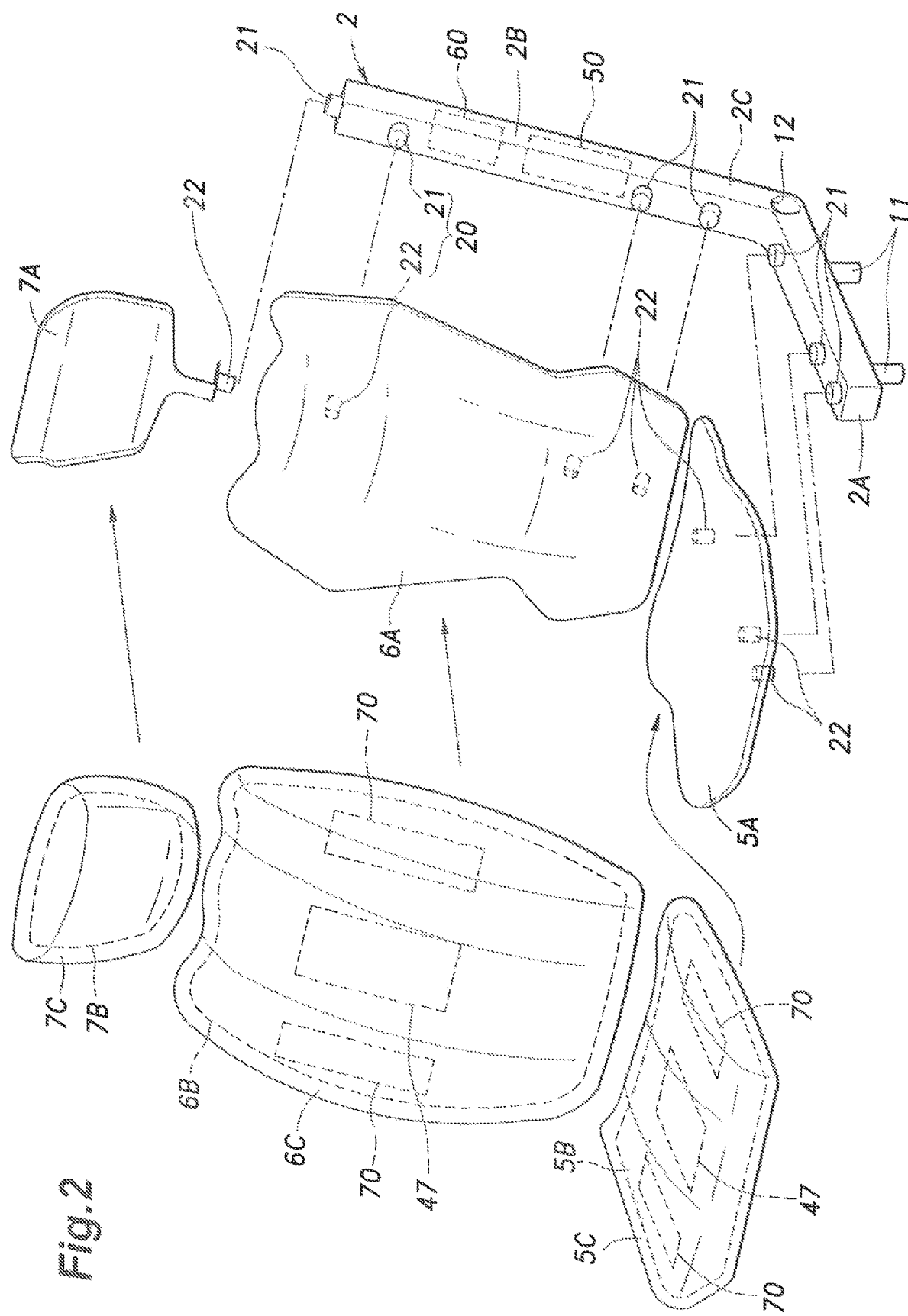
FIG. 2 is an exploded perspective view of the vehicle seat.
Figure 3:
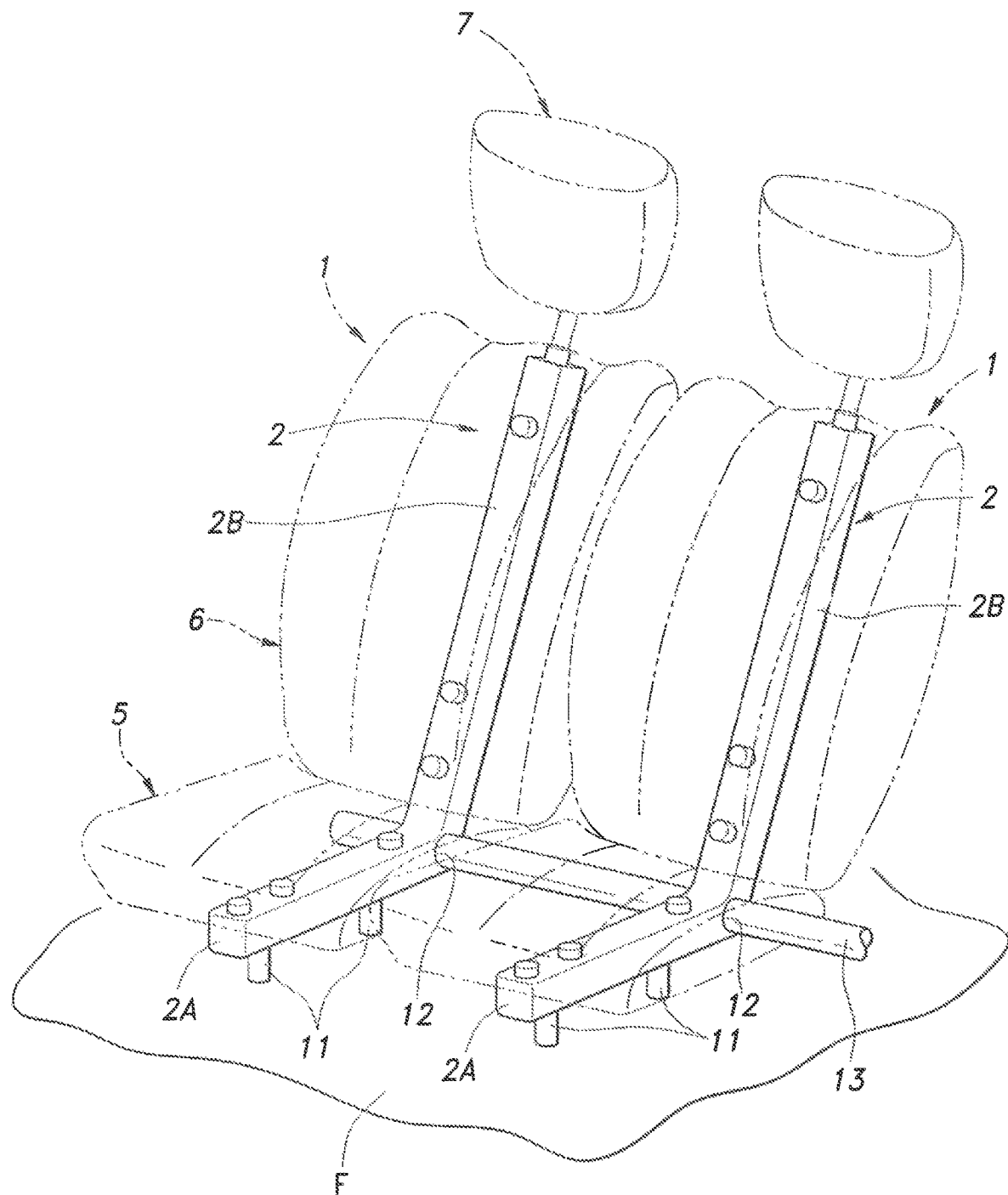
FIG. 3 is a perspective view of the vehicle seat formed by connecting two seat part segments.

As shown in FIGS. 1 to 3, the seat 1 includes a frame member 2 supported by a floor F of a vehicle, and seat parts that are supported by the frame member 2. The seat parts include a seat cushion 5, a seat back 6 and a head rest 7. The seat cushion 5 supports an occupant from below, and the seat back 6 extends upward from the rear end of the seat cushion 5 to support the back of the occupant. The head rest 7 extends upward from the upper end of the seat back 6 to support the head of the occupant from behind. The seat cushion 5 is provided with a sub frame 5A, a pad 5B supported by the sub frame 5A, and a skin member SC covering the pad 5B. Similarly, the seat back 6 is provided with a sub frame 6A, a pad 6B supported by the sub frame 6A, and a skin member 6C covering the pad 6B, and the head rest 7 is provided with a sub frame 7A, a pad 7B supported by the sub frame 7A, and a skin member 7C covering the pad 7B. In the illustrated embodiment, each sub frame is made of a sheet member or a plate member made of metal or plastic material.

The frame member 2 includes a lower frame part 2A extending in a fore and aft direction, and an upper frame part 2B extending substantially upward from the rear end of the lower frame part 2A. The lower frame part 2A and the upper frame part 2B are each made of a hollow tubular member defining an inner space 2C. In the illustrated embodiment, each tubular member is provided with a rectangular cross section, but may also be provided with a circular, polygonal or any other shape. The lower frame part 2A is attached to the floor F via a plurality of legs 11. These legs 11 may be either directly attached to the floor F or via a slide rail system that allows the fore and aft adjustment of the seat 1. As shown in FIG. 3, the rear end of the lower frame part 2A is formed with a connecting hole 12 passed laterally across the lower frame part 2A. A plurality of similar seats may be joined to each other by using a connecting member 13 extending laterally and passed into the connecting holes 12 of the seats or seat segments to be connected to each other. The connecting member 13 may be attached to the floor F via a bracket (not shown in the drawings), for instance.

As shown in FIG. 2, the seat cushion 5, the seat back 6 and the head rest 7 are both mechanically and electrically (or optically) connected to the frame member 2 via a connector unit 20. The connector unit 20 includes a plurality of frame side connectors 21 and corresponding seat part side connectors 22 provided on the respective seat parts.

Figure 4:
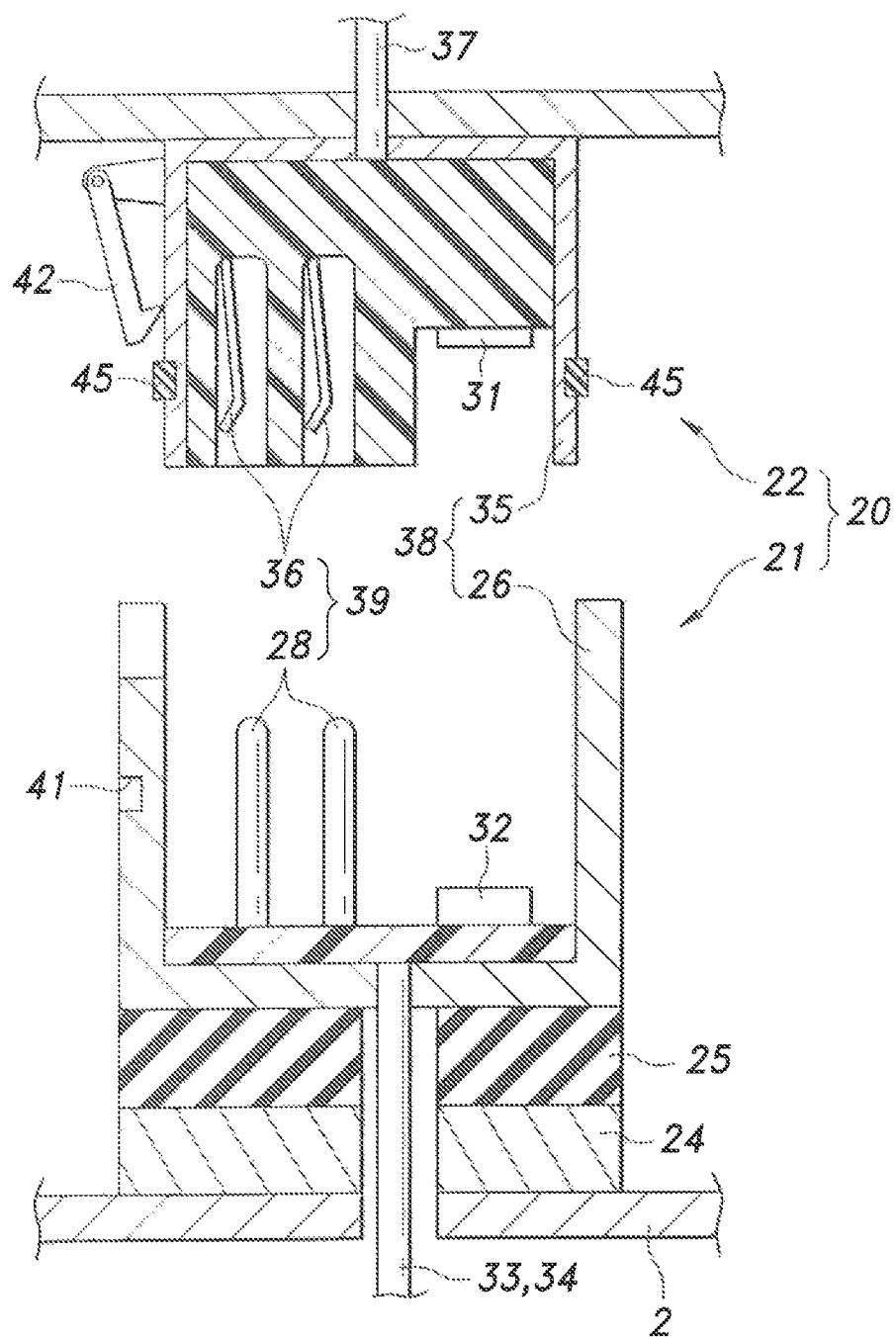
FIG. 4 is a sectional view of a connector unit of the vehicle seat.

As shown in FIG. 4, each frame side connector 21 includes a base portion 24 attached to the frame member 2, and a first tube 26 supported by the base portion 24 via a cushion element 25. The base portion 24 is attached to the frame member by welding or fastening. The first tube 26 has an open end facing away from the frame member and a closed bottom end.

The cushion element 25 may consist of an elastic member such as rubber. Alternatively, the cushion element 25 may consist of an air damper, an electromagnetic damper, an oil damper or the like. When the cushion element 25 consists of an air damper, the air damper may be provided with an air chamber which functions as an actuator by expanding and contracting by the supply and the release of compressed air into and out of the air chamber. The air chamber may be expanded and contracted by receiving and releasing air according to the vibrations transmitted from the vehicle so as to function as an active damper (active suspension system) that cancels the vibrations of the vehicle. The oil damper may consist of a viscoelastic variable damper.

The bottom end of the first tube 26 is internally provided with first connecting members 28 for electrically or optically connecting to counterparts (which will be described hereinafter) provided on the corresponding seat part, and a recognition device 32 for identifying an identifier 31 (which will be described hereinafter). The lead wires of the first connecting members 28 and the recognition device 32 are bundled together, and extend into the frame member 2 through the bottom end of the first tube 26, the cushion element 25 and the base portion 24.

Each seat part side connector 22 includes a second tube 35 connected to the corresponding sub frame 5A, 6A, 7A. The second tube 35 has an open end facing away from the corresponding sub frame 5A, 6A, 7A and a closed bottom end remote from the open end.

The bottom end of the second tube 35 is internally provided with second connecting members 36 for electrically or optically connecting to the corresponding first connecting members 28, and an identifier 31. The wiring connected to the second connecting members 36 extends into the corresponding seat part (5, 6, 7) through the bottom end of the second tube 35 and the sub frame 5A, 6A, 7A.

In the illustrated embodiment, the second tube 35 is configured to fit into the first tube 26. In other words, the first tube 26 is an outer tube, and the second tube 35 is an inner tube. Alternatively, the first tube 26 may be an inner tube while the second tube 35 is an outer tube. A locking recess 41 is formed on the outer surface of the first tube 26, and a locking claw 42 is pivotally provided on the outer surface of the second tube 35 so that the first tube 26 and the second tube 35 may become attached to each other by the locking claw 42 engaging the locking recess 41. The locking claw 42 is urged by a biasing member such as a torsion coil spring (not shown in the drawings) into engagement with the locking recess 41. By manually operating the locking claw 42, the first tube 26 and the second tube 35 can be detached from each other. If desired, the first tube 26 and the second tube 35 may be provided with a non-circular cross section such as a polygon and an ellipsis so that the first tube 26 and the second tube 35 may not be rotated around the axial line relative to each other. The first tube 26 and the second tube 35 which can be detachably connected to each other thus jointly form a mechanical connector 38 for mechanically connecting the corresponding seat part to the frame member 2.

An annular seal member 45 is retained on the outer periphery of the second tube 35 to provide a liquid tight seal between the outer circumferential surface of the second tube 35 and the inner circumferential surface of the first tube 26.

When the first tube 26 and the second tube 35 are connected to each other, the first connecting members 28 and the second connecting members 36 are electrically or optically connected to each other. The first connecting member 28 and the second connecting member 36 may consist of electric connectors that are electrically connected to each other by contact, optical fiber connectors that are optically connected each other when connected, or coils or other devices that are magnetically connected to each other without contact. When the first tube 26 and the second tube 35 are connected to each other, the first connecting member 28 and the second connecting member 36 are positioned inside the second tube 35.

When the first tube 26 and the second tube 35 are connected to each other, the recognition device 32 opposes the identifier 31 so that the recognition device 32 recognizes the identifier 31. The identifier may consists of image information such as a bar code or an IC tag, the recognition device 32 may consist of a camera that can read image information such as a bar code or an IC tag reader for reading IC tags. The information contained in the identifier 31 may be information on the size and shape of the corresponding seat part, or information on an electric component 47 provided on the corresponding seat part.

As shown in FIG. 2, each seat part is preferably connected to the frame member 2 via a plurality of connector units 20 such that the seat part is prevented from rotating relative to the frame member 2. In the illustrated embodiment, the seat cushion 5 and the seat back 6 are each connected to the frame member 2 via three connector units 20. The connectors 22 on each seat part 5, 6, 7 are each positioned laterally central part thereof. Thus, the frame member 2 is positioned laterally centrally with respect to the seat part 5, 6 and 7.

Figure 5:
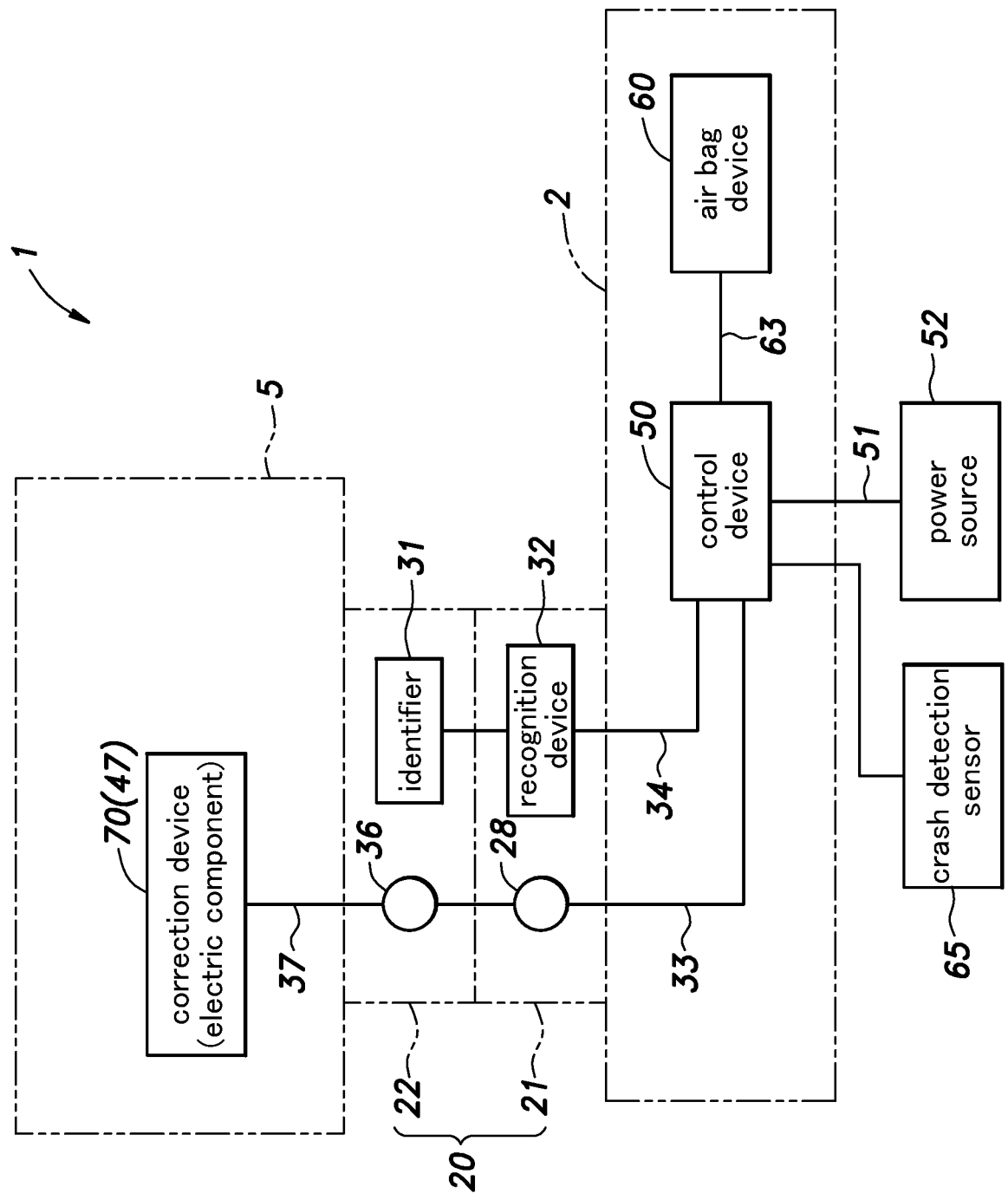
FIG. 5 is a block diagram of the internal structure of the vehicle seat.

As shown in FIGS. 2 and 5, the inner space 2C of the frame member 2 receives a control device 50 which is one form of electric device. The control device 50 consists of an electronic control unit comprising a circuit board supporting CPU, memory and other components and fixedly attached to the inner surface of the frame member 2. The control device 50 is connected to an onboard power source 52 via a power cable 51. The power cable 51 extends to the power source 52 via the inner space 2C of the frame member 2 and the interior of one of the legs 11. The control device 50 is connected to the first connecting members 28 and the recognition devices 32 of the frame side connectors 21 via signal wires 33 and 34. If the cushion element 25 consists of an active element such as an air damper, the control device 50 is connected the cushion element 25 via signal wires. In an alternate embodiment, the frame member 2 is made of electrically insulating material, and the circuit pattern of the control device 50 is directly provided on the inner surface of the frame member 2. In such a case, the frame member 2 and the control device 50 may be combined into a single integral component so that the number of component parts can be reduced, and weight reduction can be accomplished.

Each seat part may be provided with an electric component 47 which may consist of any electric component such as a heater, a cooling fan, a temperature sensor, a humidity sensor, a pressure, an air bag, a switch and an actuator. The electric component 47 may be provided between the sub frame 5A, 6A, 7A and the pad or between the pad and the skin member SC, 6C, 7C. The electric component provided on the seat part is electrically connected to the second connecting member via wires 37, and thence to the control device 50 via the connector unit 20 and the signal wires 33.

In the illustrated embodiment, each seat part can be interchangeably selected from a number of selections having different sizes and configurations, different properties of the pad and the skin member, and the kinds of the electric component 47, and connected to the frame member 2 via the connector unit 20. For instance, the seat cushion 5, the seat back 6 and the head rest 7 can be selected from preselected standard products based on the standard body sizes and shapes of an adult male, an adult female, a child and an infant.

The inner space 2C of the upper frame part 2B receives an air bag device 60 which includes a folded air bag and an inflator for inflating the air bag at the time of a crash. A rear end of the upper frame part 2B is provided with an opening through which the air bag can be deployed. This air bag is intended to protect an occupant seated in a seat behind the seat in question from hitting the seat in question. Because the air bag device is provided directly on the frame member 2 having a relatively high stiffness, instead of the seat part, the air bag can be deployed in a stable manner. The opening may be provided with a lid that is configured to the displaced or fractured under the pressure from the deploying air bag.

The inflator of the air bag is electrically connected to the control device 50 via wires 63 passed through the inner space 2C of the frame member 2. The control device 50 is configured to activate the air bag device 60 according to a signal from a crash detection sensor 65 such as an acceleration sensor.

Side parts of the seat cushion 5 and the side parts of the seat back 6 are each provided with a correction device 70 for forcing the occupant to a proper seating posture at the time of a vehicle crash. The proper seating posture means that the occupant's buttocks are centrally positioned on the seat cushion 5 and the occupant's back is also centrally positioned on the seat back 6, both laterally and longitudinally, so that the occupant may withstand the deceleration of a vehicle crash in an optimum fashion. Each correction device 70 may include an air cylinder for moving the corresponding part of the seat part. The correction device 70 may be considered as a form of the electric component 47, and is electrically connected to the corresponding second connecting member 36 via wires 37 to be connected to the control device 50 via the connector unit 20. The control device 50 controls the correction device 70 according to the signal from the crash detection sensor 65.

Thus, the seat parts such as the seat cushion 5, the seat back 6 and the head rest 7 can be detachably attached to the frame member 2 so that the seat 1 can be adapted to the occupant simply by selecting the seat parts accordingly.

Because the connector unit 20 allows the seat parts to be both electrically and mechanically connected to the frame member 2, installing and replacing the seat parts can be accomplished in an effortless manner.

Because each connector unit 20 can be connected by fitting the second tube 35 into the first tube 26, the first connecting member 28 and the second connecting member 36 are protected from damages owing to an external force and contamination by moisture and other foreign matters.

The control device 50 identifies each identifier 31 with the corresponding recognition device 32 so that the control device 50 is able to acquire information on the particular seat part connected to the frame member 2. Therefore, the control device 50 is enabled to control the electric component 47 incorporated in the corresponding seat part in a correct manner.

Each connector unit 20 may be configured to transmit both signals and electric power between the control device 50 provided on the frame member 2 and the electric component 47 incorporated in each seat part via the corresponding connector unit 20.

Figure 6:
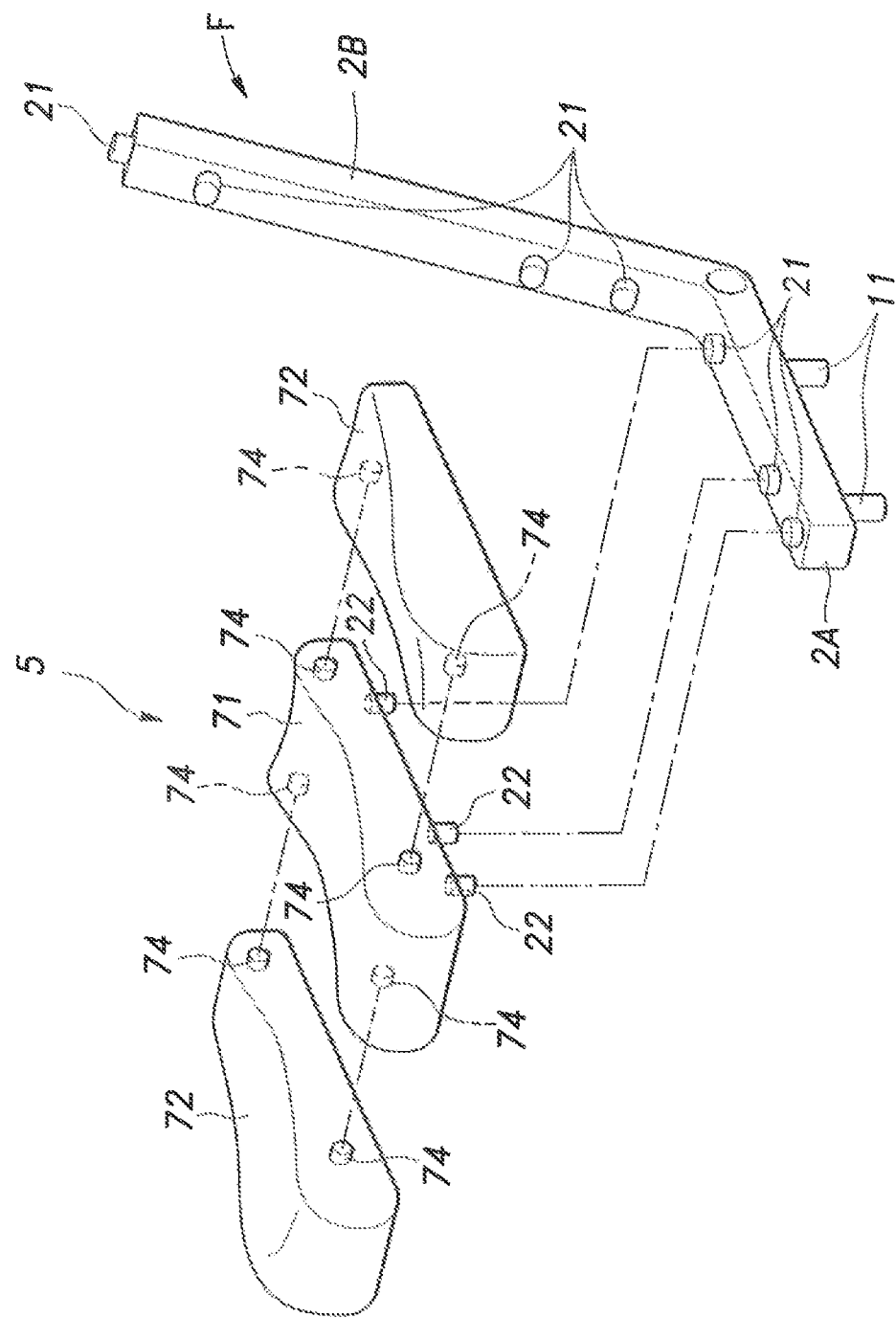
FIG. 6 is an exploded perspective view of a vehicle seat given as a modification of the vehicle seat of the first embodiment.

In a modified embodiment, at least one of the seat parts consist of a plurality of seat part segments. For instance, as shown in FIG. 6, the seat cushion 5 may consist of a laterally central part 71 and a pair of side parts 72 detachably connected to either side of the central part 71. The central part 71 and the side parts 72 are each provided with a sub frame, a pad and a skin member, individually. The central part 71 is detachably connected to the frame member 2 via a first connector unit 20. Each side part 72 is detachably connected to the central part 71 via a second connector unit 74 which connects the two parts both mechanically and electrically, and may be similar to the aforementioned connector units 20. Each of the central part 71 and the side parts 72 may be provided with an electric component 47. The electric component 47 provided on either one of the side parts 72 may be connected to the control device 50 provided in the frame member 2 via the second connector unit 74, the central part 71 and the first connector unit 20.

In the foregoing embodiment, the first tube 26 of at least one of the connector units 20 may be connected to the base portion 24 via a hinge, a ball joint or any other movable joint. Also, a resilient member may be provided on any of the connector units 20 for urging the first tube 26 to an initial position relative to the corresponding base portion.

Figure 7:
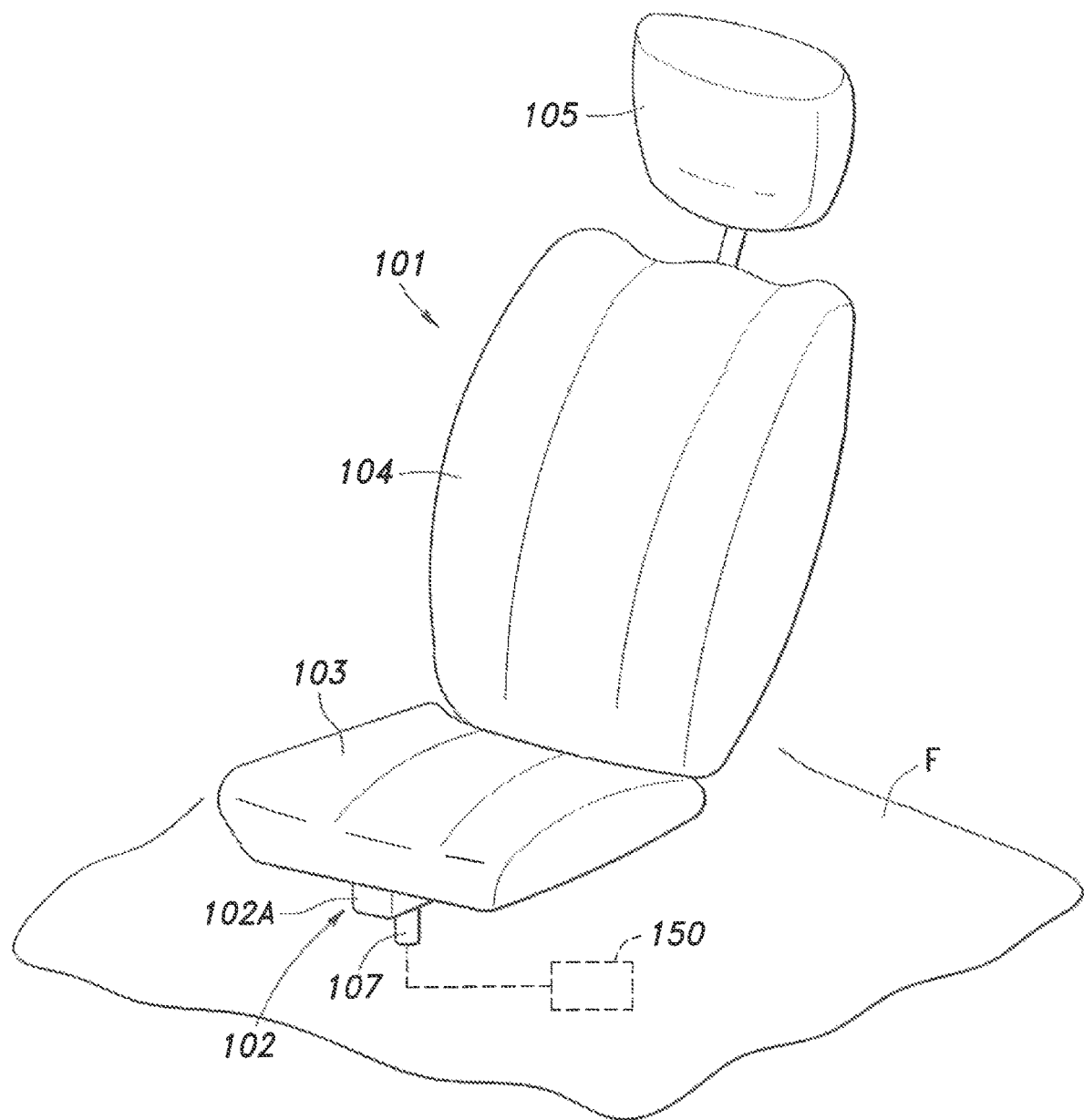
FIG. 7 is a perspective view of a vehicle seat according to a second embodiment of the present invention.
Figure 8:
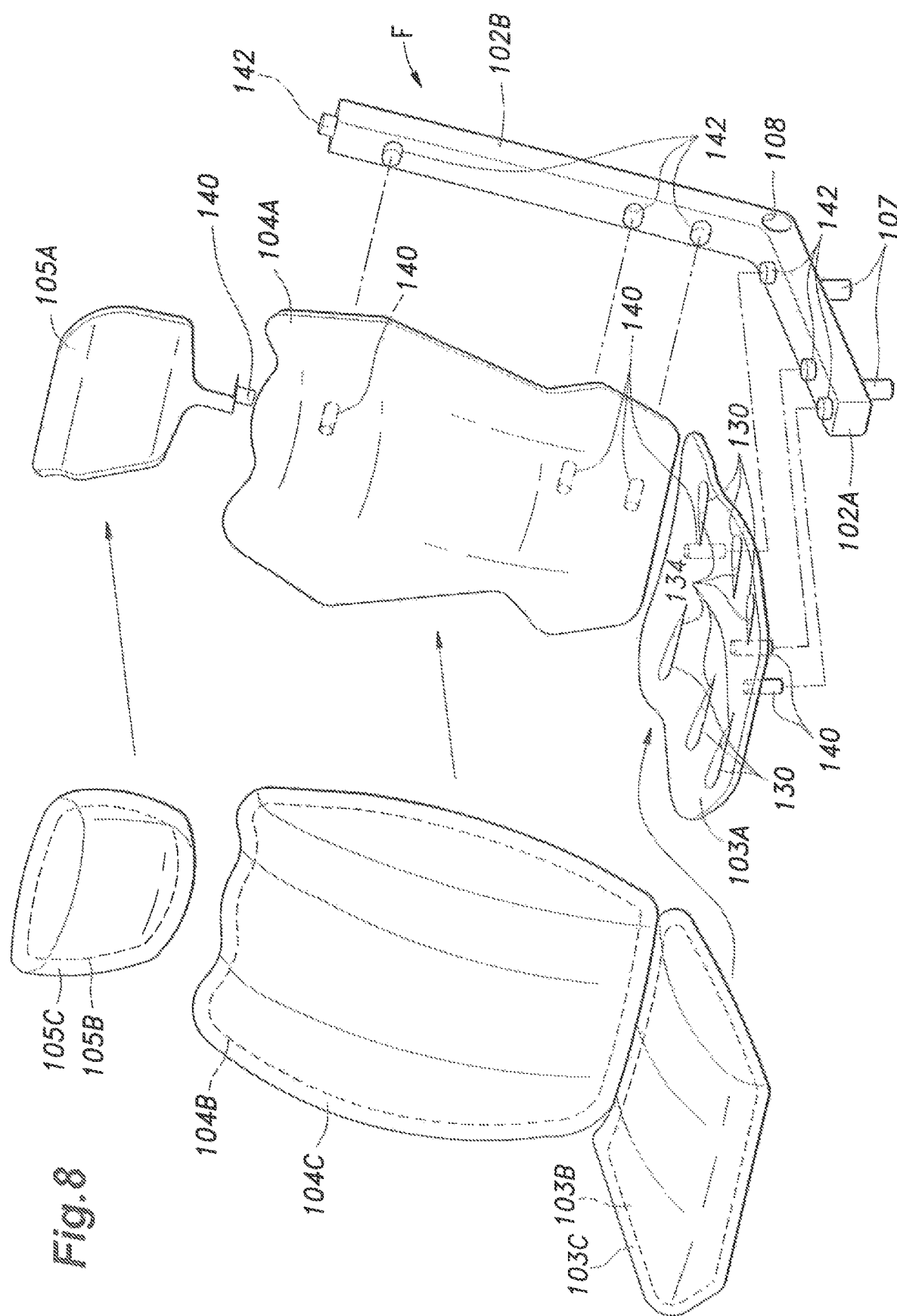
FIG. 8 is an exploded perspective view of the vehicle seat.
Figure 9:
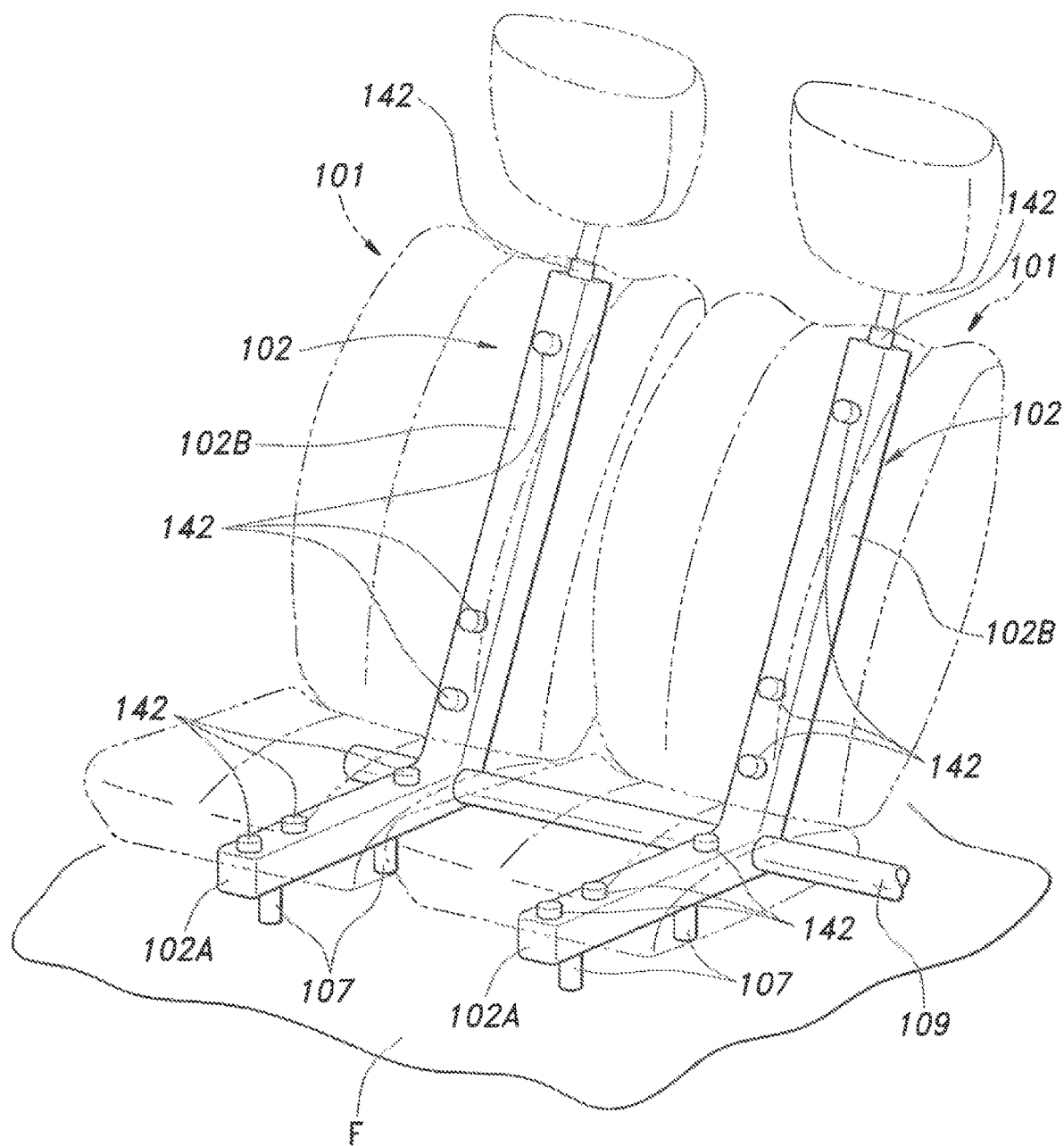
FIG. 9 is a perspective view of the vehicle seat formed by connecting two seat segments.

FIGS. 7 to 11 show a second embodiment of the present invention. As shown in FIGS. 7 to 9, the seat 101 includes a frame member 102 supported by a floor F of a vehicle, and seat parts that are supported by the frame member 102. The seat parts include a seat cushion 103, a seat back 104 and a head rest 105. The seat cushion 103 supports an occupant from below, and the seat back 104 extends upward from the rear end of the seat cushion 103 to support the back of the occupant. The head rest 105 extends upward from the upper end of the seat back 104 to support the head of the occupant from behind. The seat cushion 103 is provided with a sub frame 103A, a pad 103B supported by the sub frame 103A, and a skin member 103C covering the pad 103B. Similarly, the seat back 104 is provided with a sub frame 104A, a pad 104B supported by the sub frame 104A, and a skin member 104C covering the pad 104B, and the head rest 105 is provided with a sub frame 105A, a pad 105B supported by the sub frame 105A, and a skin member 105C covering the pad 105B. In the illustrated embodiment, each sub frame is made of a sheet member or a plate member made of metallic or plastic material.

The frame member 102 includes a lower frame part 102A extending in a fore and aft direction, and an upper frame part 102B extending substantially upward from the rear end of the lower frame part 102A. The lower frame part 102A and the upper frame part 102B are each made of a hollow tubular member. In the illustrated embodiment, each tubular member is provided with a rectangular cross section, but may also be provided with a circular, polygonal or any other shape. The lower frame part 102A is attached to the floor F via a plurality of legs 107. As shown in FIG. 3, the rear end of the lower frame part 102A is formed with a connecting hole 108 passed laterally across the lower frame part 102A. A plurality of similar seats may be joined to each other by using a connecting member 109 extending laterally and passed into the connecting holes 108 of the seats to be connected to each other. The connecting member 109 may be attached to the floor F via a bracket (not shown in the drawings), for instance.

Figure 10:
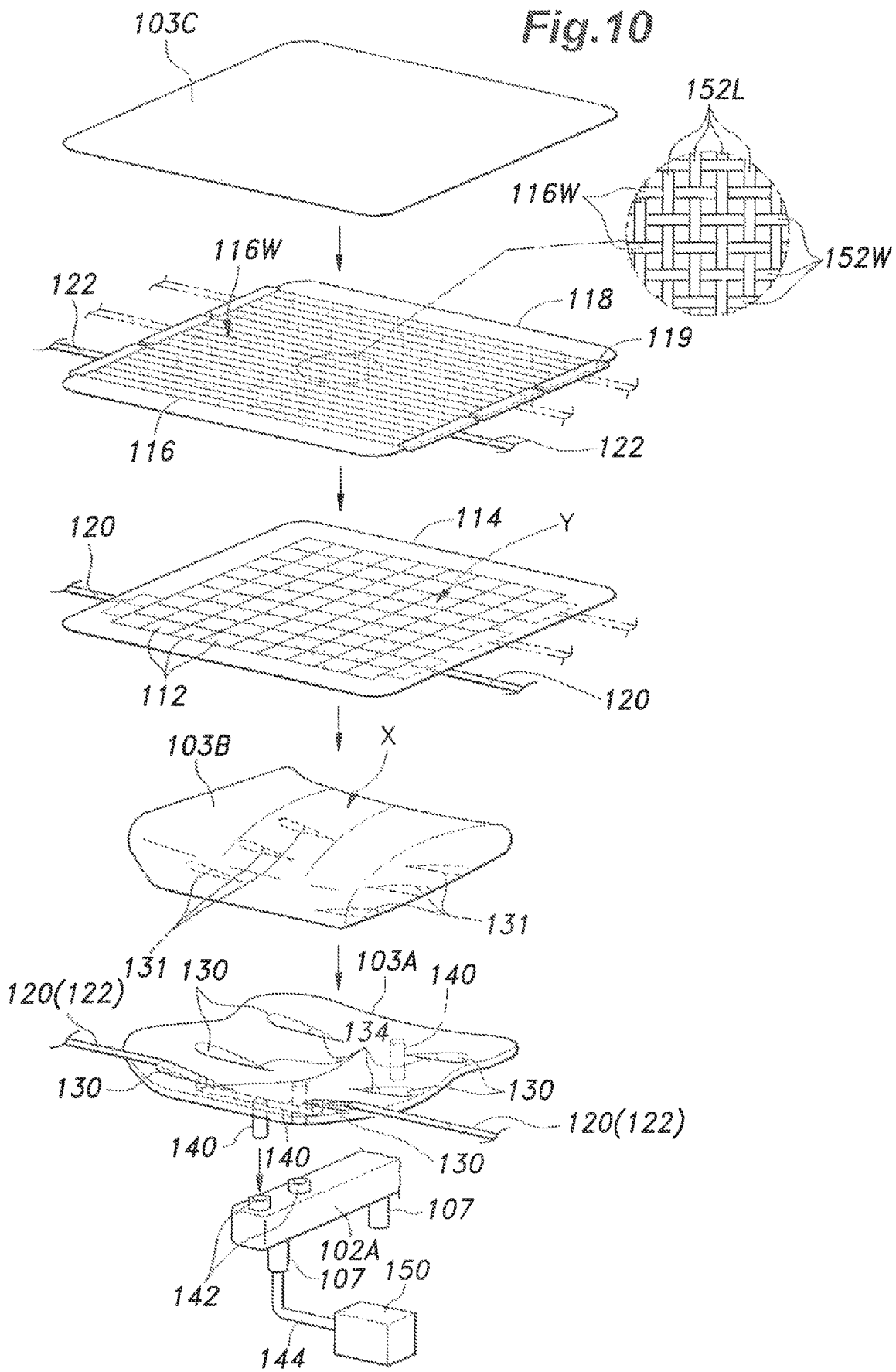
FIG. 10 is an exploded perspective view of a seat cushion of the vehicle seat.
Figure 11:
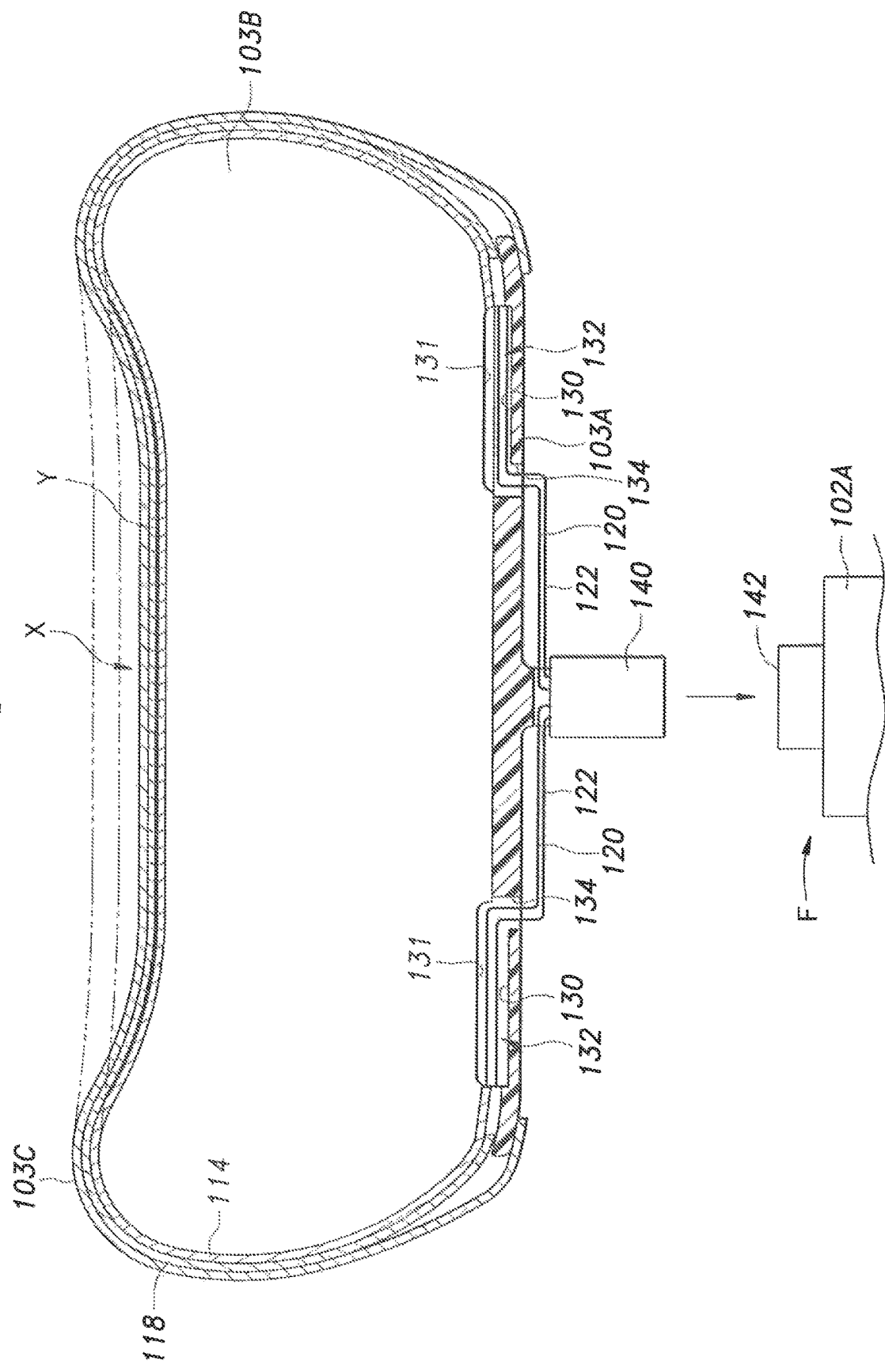
FIG. 11 is a cross sectional view of the seat cushion.

As shown in FIG. 10, a pressure sensor sheet 114 for detecting a pressure applied thereto and an actuator sheet 118 for changing the stiffness (softness) of the seat cushion 103 are interposed between the skin member 103C and the pad 103B of the seat cushion 103. In an embodiment of the present invention, the pressure sensor sheet 114 and the actuator sheet 118 are incorporated in a single sheet. The pressure sensor sheet 114 and the actuator sheet 118 are primarily formed of fabric sheets, and cover the upper surface or the support surface X of the pad 103B supporting the load from the occupant. As the pressure sensor sheet 114 and the actuator sheet 118 extend along the support surface X, the pressure sensor sheet 114 detects the load acting on the support surface X, and the actuator sheet 118 changes the stiffness of the seat cushion 103 immediately under the support surface X.

The pressure sensor sheet 114 includes a plurality of pressure sensors 112 arranged over a detection surface Y of the pressure sensor sheet 114 in a grid pattern and each consisting of a device that changes an electric property such as resistance and capacitance according to the load applied perpendicularly on the detection surface Y of the pressure sensor sheet 114. By analyzing the output signals from the individual pressure sensors 112, the distribution of the pressure applied to the detection surface Y can be obtained. In the illustrated embodiment, the pressure sensor sheet 114 includes a substrate consisting of a film, lower electrodes arranged on the film in the grid pattern, electroconductive rubber material deposited on the upper surfaces of the lower electrodes, and upper electrodes opposing the lower electrodes via the electroconductive rubber material. The upper electrodes and the lower electrodes each consisting of a square film having a side measuring a few millimeters to a few centimeters oppose each other with a gap in the order of a few millimeters defined therebetween. The electric resistance of the rubber material between each upper electrode and the corresponding lower electrode changes in dependence on the pressure applied to the upper electrode in a direction perpendicular to the detection surface Y. Since the pressure sensor sheet 114 consists of a flexible sheet, the pressure sensor sheet 114 can conform to the surface contour of the support surface X which changes depending on the load applied thereto by the occupant. The pressure sensor sheet 114 is not limited to the one described here, but may consist of any other pressure sensor in the form of a sheet, such as a piezoelectric sensor sheet having piezoelectric fibers woven therein, and a capacitive sensor sheet including a deformable film interposed between a pair of electrodes. Lead wires 120 connected to the individual pressure sensors 112 extend from side edges of the pressure sensor sheet 114 (three wires from each lateral edge in the illustrated embodiment).

The actuator sheet 118 includes a plurality of laterally extending linear soft actuator 116W, a plurality of warps 152L made of fibers and a plurality of woofs 152 W also made of fibers. Each soft actuator 116W consists of a filament that extends laterally across the actuator sheet 118 and shrinks depending on a voltage applied thereto. In the illustrated embodiment, each soft actuator 116W is made of a shape memory alloy, and has a diameter of several tens of micrometers to several hundreds of micrometers. The soft actuator 116W may also consist of electroconductive high polymer, carbon-based material or magnetic fluid that changes shape according to a magnetic field created by an applied voltage. As shown in the enlarged view of FIG. 10, the soft actuators 116W are woven with the warps 152L. Therefore, the soft actuators 116W can be arranged along the surface of the actuator sheet 118 without any difficulty, and are prevented from moving within the actuator sheet 118.

A plurality of sheet connectors 119 are arranged along the lateral edges of the actuator sheet 118. The soft actuators 116W are electrically connected to these sheet connectors 119.

The pressure sensor sheet 114 and the actuator sheet 118 cover the pad 103B, and are attached to the sub frame 103A at the peripheral edges thereof by being interposed between the sub frame 103A and the pad 103B. The effective detecting area of the pressure sensor sheet 114 or the detection surface Y may be provided only on the part of the pressure sensor sheet 114 covering the upper surface of the pad 103B. In the illustrated embodiment, the actuator sheet 118 adjoins the skin member 103C. The sheet connectors 119 are connected to lead wires 122.

In particular, the soft actuator sheet 118 is fixedly attached to the sub frame 103A via the sheet connectors 119 in the illustrated embodiment. When an electric voltage is applied to the soft actuator sheet 18, the tension in the soft actuator sheet 118 increases. As a result, the support surface X may be elevated as a result as shown by the imaginary lines in FIG. 11. When the tension in the soft actuator sheet 118 increases, the reaction to the downward load on the seat cushion 103 for a given load increases. In other words, the stiffness of the support surface X of the seat cushion 103 increases. Thus, the stiffness or rigidity of the support surface X of the seat cushion 103 can be changed by applying a different voltage to the soft actuator sheet 118.

The upper surface of the sub frame 103A is provided with a plurality of grooves 130 (six grooves in the illustrated embodiment) each extending from a lateral edge to a laterally central part of the sub frame 103A. The grooves 130 extending from either lateral edge are aligned in pairs. The pad 103B is provided with recesses 131 opposing the respective grooves 130 so that laterally extending passages 132 are defined between the pad 103B and the sub frame 103A. The wires 120 and 122 are passed through these passages 132 so that the occupant seated on the seat cushion 103 is prevented from experiencing any discomfort owing to the presence of the wires 120 and 122, and the external appearance of the seat 101 can be enhanced.

The inner end of each groove 130 is formed with a through hole 134 passed through the sub frame 103A, and the wires 122 and 122 are received in the groove 130 and passed through the through hole 134. The upper surface of the frame lower part 102A are provided with first connectors 142 which project upward. A plurality of second connectors 140 that are configured to be connected to the corresponding first connectors 142 provided on the frame lower part 102A are attached to or otherwise provided on central parts of the lower surface of the sub frame 103A. The wires 120 and 122 extending out of the through holes 134 are connected to terminal pieces of the second connectors 140.

The first connectors 142 that project upward are configured to be mechanically and electrically connected to the corresponding second connectors 140 that project downward. Wires 144 connected to terminal pieces of the first connectors 142 are passed through the inner space 102C of the frame lower part 102A, and are connected to a control device 150 provided on an appropriate part of the floor F.

The control device 150 consists of an electronic control unit provided with a central processing unit and memory, and, as shown in FIG. 10, is connected to the pressure sensors 112 and the soft actuators 116W via the wires 120, 122 and 144. The control device 150 is configured to detect the pressures applied to the pressure sensors 112 from the changes in the electric properties of the respective pressure sensors 112. The control device 150 further applies appropriate voltages to the respective soft actuators 116W according to the magnitude and the distribution of the pressure applied to the pressure sensors 112.

The mode of operation of the seat 101 is described in the following. The occupant in the seat 101 applies uneven pressure to the support surface X of the seat cushion 103. For instance, a rear part of the support surface X receives a greater pressure from the buttocks of the occupant while a front part of the support surface X receives a relatively small pressure. Therefore, it is desirable if the rear part of the seat cushion 103 is made softer than the front part of the seat cushion 103.

The control device 150 computes the distribution of pressure on the detection surface Y according to the output signals from the pressure sensors 112. At this time, the detection surface Y is divided into a plurality of rectangular areas, for instance 10 by 10 rectangular areas, and the pressure applied to each rectangular area is compared with the average value of the pressure applied to the entire detection surface Y. The control device 150 drives the soft actuator 116W located under each rectangular area according to the difference between the pressure applied to this particular rectangular area and the average pressure. For instance, when the pressure applied to a certain rectangular area is greater than the average pressure value, the soft actuator 116W located under this rectangular area is extended so that this rectangular area is made comparatively softer. Conversely, when the pressure applied to a certain rectangular area is smaller than the average pressure value, the soft actuator 116W located under this rectangular area is contracted so that this rectangular area is made comparatively harder or stiffer. By thus adjusting the softness or the stiffness of the different parts of the support surface X, the sitting comfort for the occupant can be enhanced.

In this embodiment, each rectangular area may consist of a square having a side which may range between several millimeters to several centimeters, and such squares are arranged in a grid pattern. Therefore, the distribution of pressure on the detection surface Y can be detected with a corresponding resolution. Also, because the soft actuators are in a linear form having a diameter that may range between several tens of micrometers and several hundreds of micrometers, the distribution of the stiffness or softness of the support surface X can be controlled with a corresponding resolution.

In the illustrated embodiment, the soft actuators 116W are arranged in the longitudinal direction (in the fore and aft direction in the case of the seat cushion 103 and in the vertical direction in the case of the seat back 104) along which the variations in the pressure from the occupant are relatively significant. More specifically, in the case of the seat cushion 103, by extending the soft actuators 116W in a rear part of the seat cushion 103 and contracting the soft actuators 116W in a front part of the seat cushion 103, the front part can be made relatively stiff while the rear part is made relatively soft. Thereby, the rear part of the seat cushion 103 is caused to sink relatively easily so that the support surface X of the seat cushion 103 is enabled to conform to the lower end of the occupant, and the comfort to the occupant can be maximized.

Because the soft actuators 116W can be electrically controlled, the softness of the seat cushion 103 can be controlled both easily and rapidly by using a simple arrangement. Because the soft actuators 116W are provided between the skin member 103C and the pad 103B, the soft actuators 116W are favorably protected from damages. Because the soft actuators 116W are positioned immediately under the skin member 103C, the support surface X of the seat cushion 103 is enabled to conform to the pressure distribution applied thereto by the occupant in a favorable manner.

By providing the pressure sensor sheet 114 immediately under the actuator sheet 118 and minimizing friction between the pressure sensor sheet 114 and the actuator sheet 118 by using suitable surface materials, the pressure sensor sheet 114 is prevented from deforming by the extension and contraction of the soft actuator sheet 116W, and enabled to detect the pressure distribution on the detection surface Y in a favorable manner.

Figure 12:
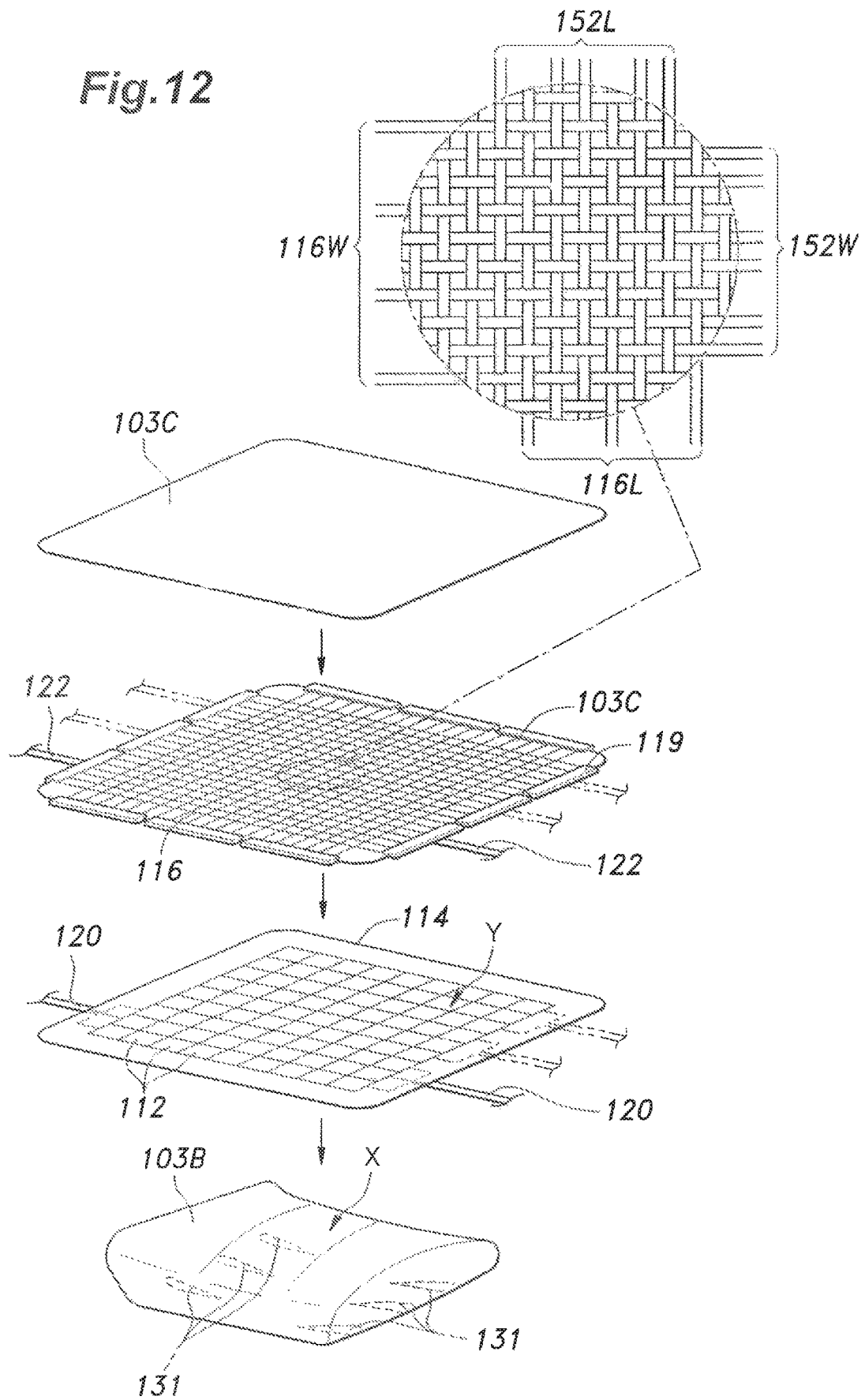
FIG. 12 is a view similar to FIG. 10 showing a seat cushion based on a modification of the second embodiment.

In a modified embodiment illustrated in FIG. 12, in addition to the laterally extending soft actuators 116W, longitudinally extending soft actuators 116L are arranged laterally. In particular, as shown in an enlarged view in FIG. 12, the laterally extending soft actuators 116W and the longitudinally extending soft actuators 116L are woven together. Therefore, the stiffness of the seat cushion 103 can be varied both along the lateral direction and the longitudinal direction or two-dimensionally. Therefore, it is possible to vary the stiffness of the seat cushion 103 in a highly localized manner. For instance, the laterally extending soft actuators 116W and the longitudinally extending soft actuators 116L in the parts of the seat cushion 103 corresponding to the ischia and/or tailbone of the occupant may be extended so as to soften the corresponding regions. Thereby, the softness distribution of the support surface X of the seat cushion 103 can be more finely adjusted. Also, because the laterally extending soft actuators 116W and the longitudinally extending soft actuators 116L are woven together, the soft actuators 116W and 116L are prevented from moving relative to each other.

In this case, the sheet connectors 119 for the longitudinally extending soft actuators 116L, are attached to the front and rear edges of the actuator sheet 118, and are also fixedly secured to the front and rear edges of the sub frame 103A either directly or via the actuator sheet 118. To accommodate the wires 122 connected to these sheet connectors 119, grooves 30 extending in the fore and aft direction may be formed in the upper surface of the sub frame 103A while the corresponding parts of the lower surface of the pad 103B of the seat cushion 103 are provided with corresponding recesses 31.

Figure 13:
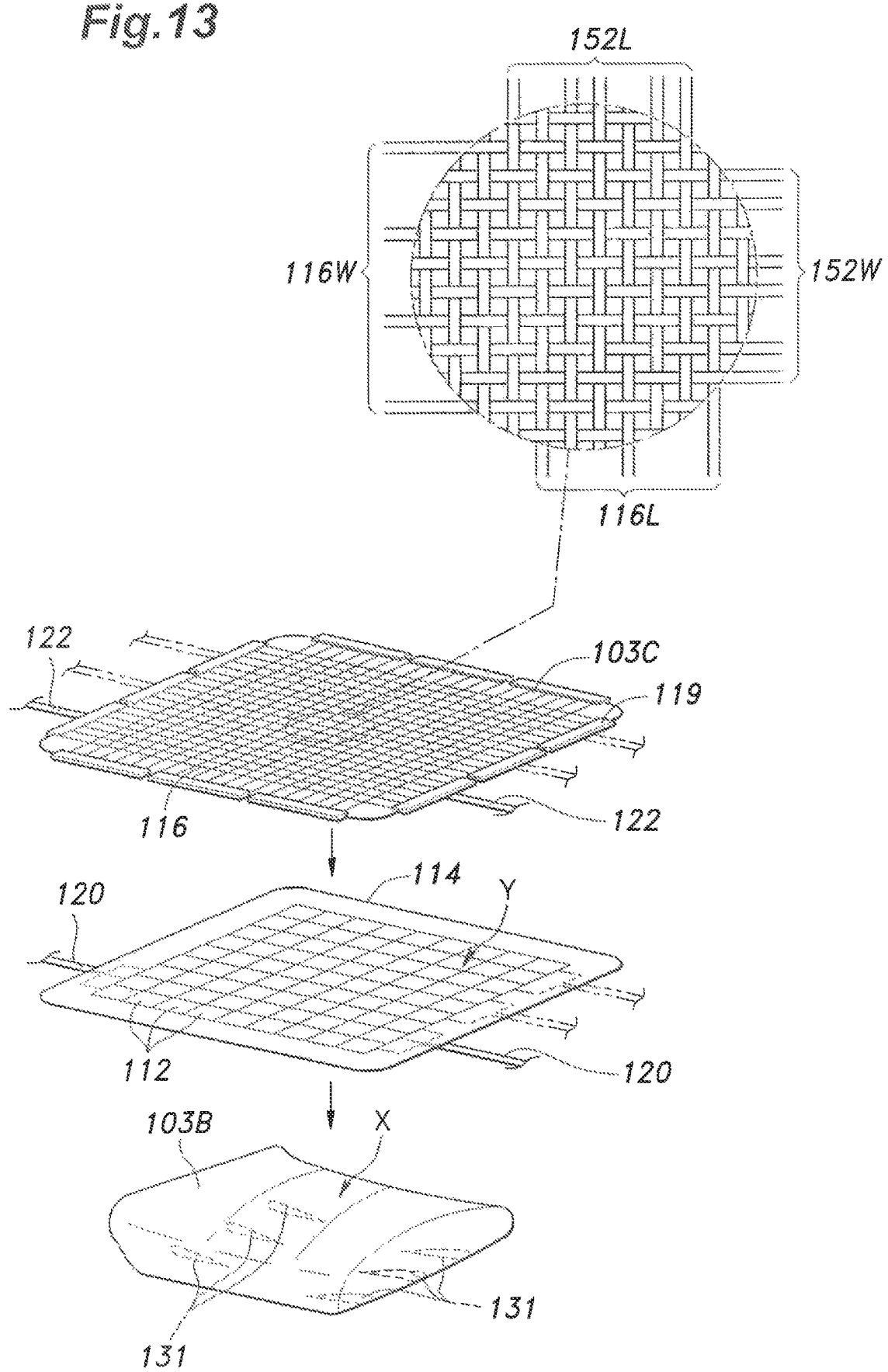
FIG. 13 is a view similar to FIG. 10 showing a seat cushion based on another modification of the second embodiment.

In another modified embodiment shown in FIG. 13, soft actuators 116W and 116L are directly incorporated in the skin member 103C. As shown in an enlarge view in FIG. 13, the soft actuators consist of laterally extending soft actuators 116W and longitudinally extending soft actuators 116L that are woven to each other as wefts and warps, respectively. The pressure sensor sheet 114 is interposed between the skin member 103C and the pad 103B. In this embodiment also, the stiffness of the seat cushion 103 can be varied both along the lateral direction and the longitudinal direction or two-dimensionally. Therefore, it is possible to vary the stiffness of the seat cushion 103 in a highly localized manner.

Because the soft actuators 116W and 116L are incorporated in the skin member 103C, the support surface X of the seat cushion 103 is enabled to conform to the pressure distribution applied thereto by the occupant in a favorable manner.

Figure 14:
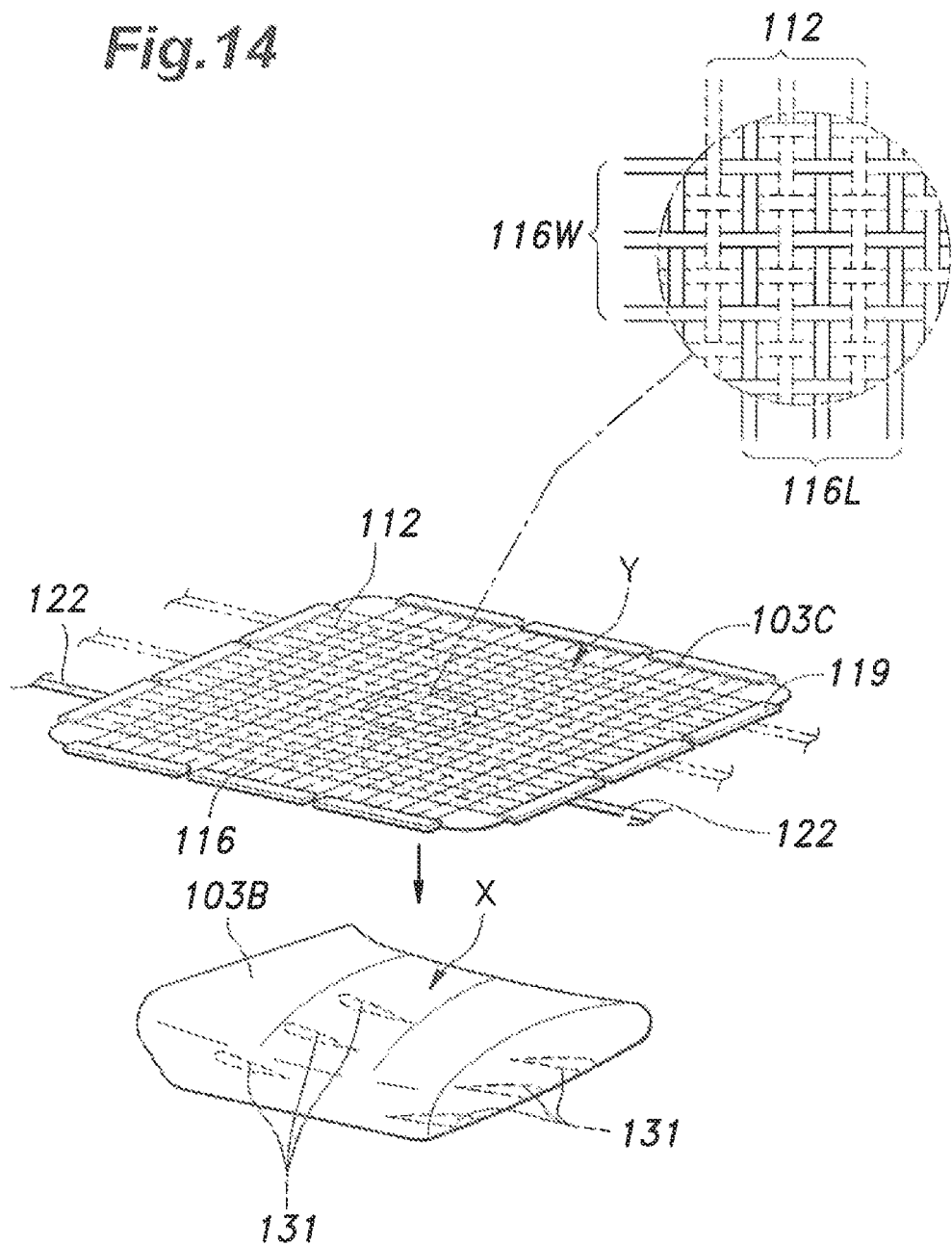
FIG. 14 is a view similar to FIG. 10 showing a seat cushion based on yet another modification of the second embodiment.

In a yet another modified embodiment shown in FIG. 14, pressure sensors 112 and soft actuators 116 in linear form are incorporated in the skin member 103C, instead of using a pressure sensor sheet 114 and an actuator sheet 118. Similarly as the embodiment illustrated in FIG. 10, the control device 150 determines the pressure distribution of the support surface X according to the signals from the pressure sensors 112, and varies the distribution of stiffness of the support surface X by extending and contracting the selected soft actuators 116 according to the determined pressure distribution. Because the pressure sensors 112 and soft actuators 116 are all incorporated in the skin member 103C, the assembly of the seat 101 is facilitated. The linear pressure sensors 112 may consist of piezoelectric fibers each including a core electrode, a flexible piezoelectric layer formed around the core electrode, and an outer electrode surrounding the piezoelectric layer.

Figure 15:
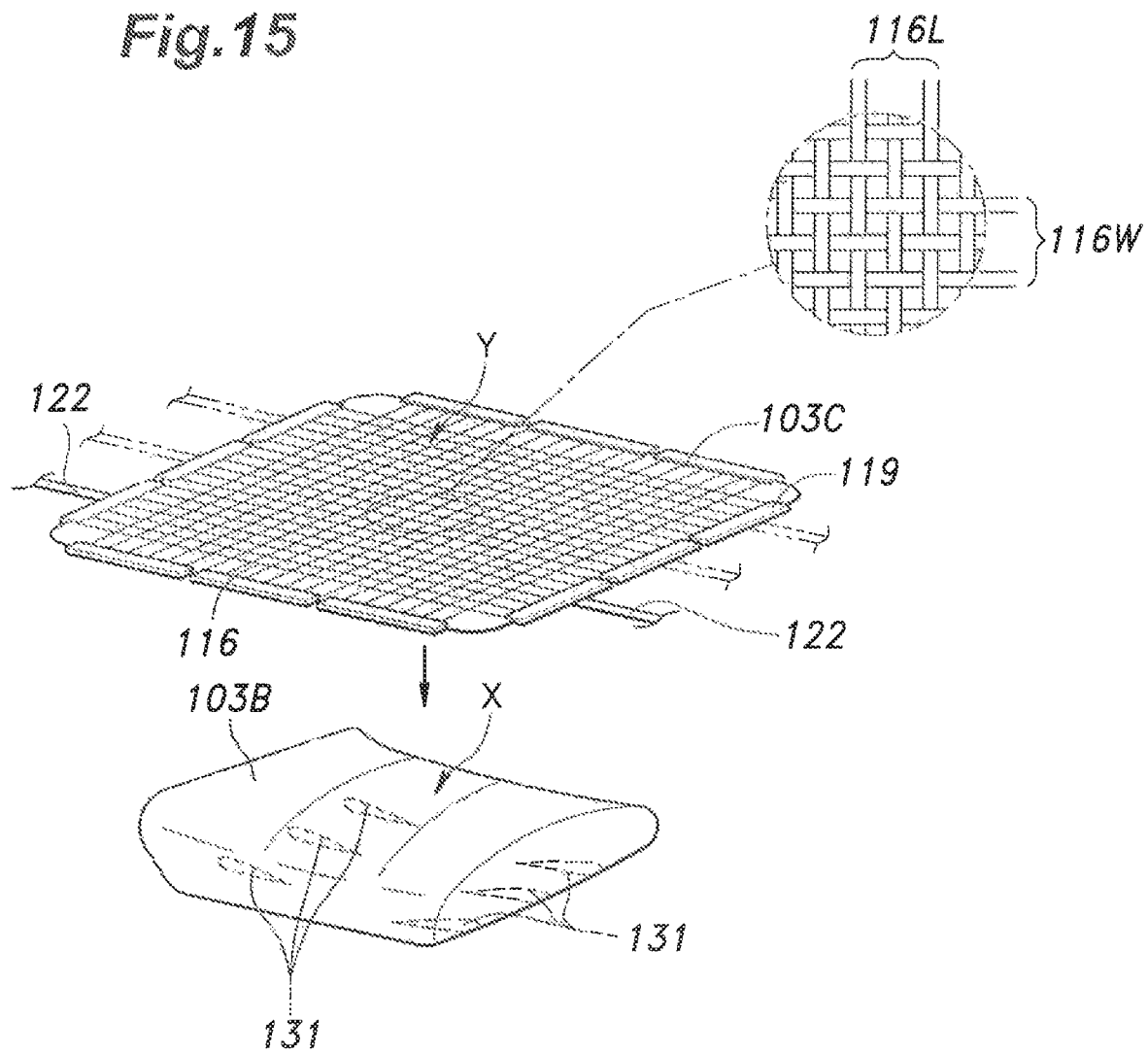
FIG. 15 is a view similar to FIG. 10 showing a seat cushion based on yet another modification of the second embodiment.

In a yet another modified embodiment shown in FIG. 15, only soft actuators 116 are incorporated in the skin member 103C, instead of using a pressure sensor sheet 114 and an actuator sheet 118. In this case, the soft actuators 116 also serve as pressure sensors 112 each by generating a voltage according to a pressure applied thereto. By thus using devices that serve both as pressure sensors and soft actuators, the number of component parts of the seat 101 can be reduced. The control device 150 determines the pressure distribution of the support surface X according to the signals from the soft actuators 116, and varies the distribution of stiffness of the support surface X by extending and contracting the selected soft actuators 116 according to the determined pressure distribution. The soft actuators 116 in this case may consist of electroconductive high polymer actuators using ionized liquid, for instance.

Figure 16:
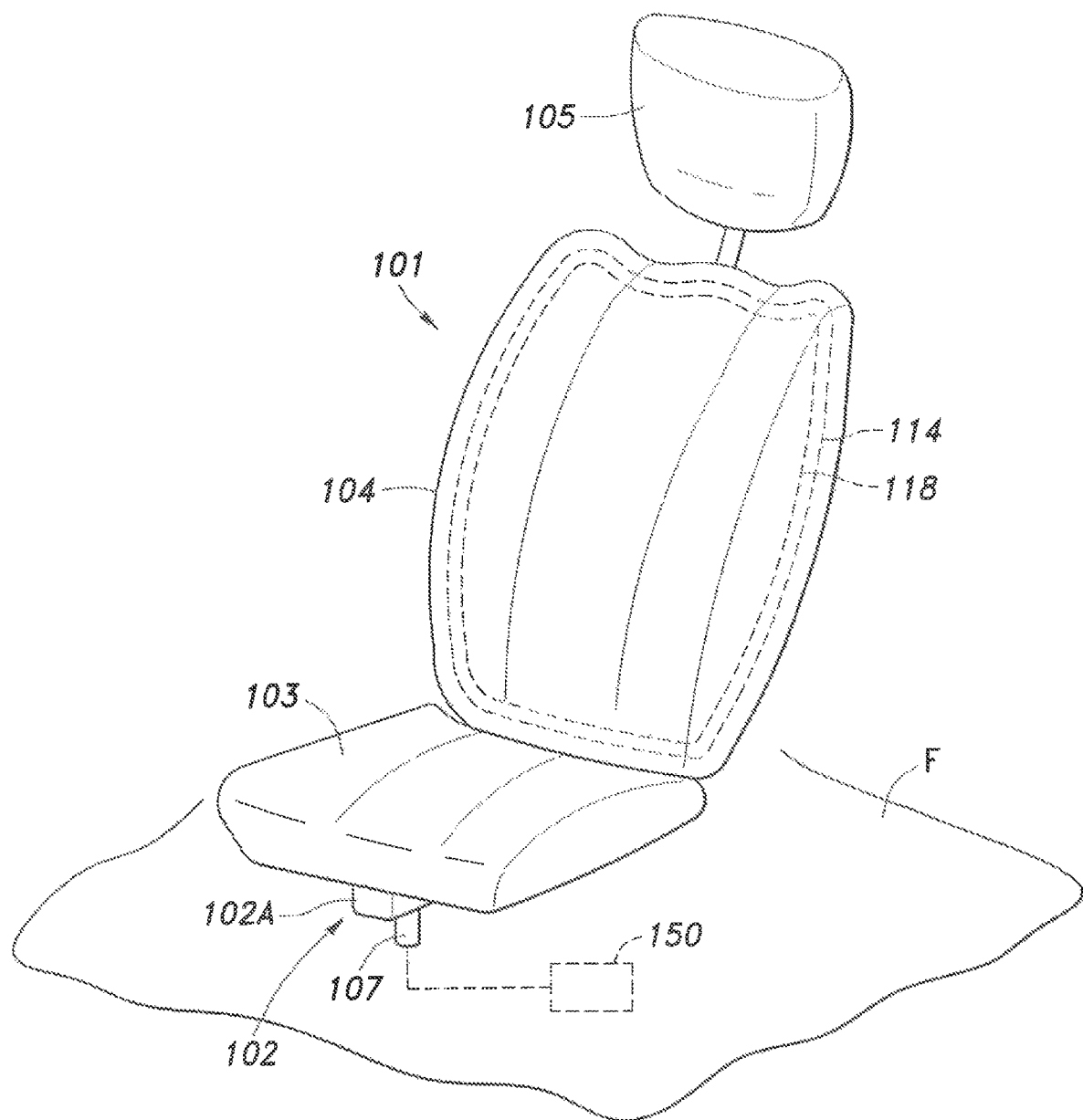
FIG. 16 is a view similar to FIG. 7 showing yet another modification of the second embodiment.

In the foregoing embodiment, the pressure sensors 112 and the soft actuators 116 are provided on the seat cushion 103, but, alternatively or additionally, may be provided on the seat back 104. In the case of this seat back 104, the pressure sensors 112 and the soft actuators 116 or the pressure sensor sheet 114 and the soft actuator sheet 118 are provided on the seat back 104 or in particular on a support surface X defined on the front surface of the pad member 104B as shown in FIG. 16. When only the laterally extending soft actuators 116W are used, laterally extending soft actuators 116W are arranged along the longitudinal direction of the seat back 104.

In the foregoing embodiments, the pressure sensors 112 are configured to detect a pressure applied perpendicularly to the support surface X, but may also detect the pressure as a tension applied to each pressure sensor 112 extending along the support surface X. Since the increase in the tension is proportional to the pressure applied perpendicularly to the support surface X, the tension provides an accurate measure of the pressure applied to the support surface X. The pressure sensor sheet 114 and the soft actuator sheet 118 may also be attached to the upper surface and/or the side surfaces of the pad 103B, instead of attaching the peripheral parts of the pressure sensor sheet 114 and the soft actuator sheet 118 to the sub frame 103A.

In the foregoing embodiments, the soft actuator sheet 118 and the pressure sensor sheet 114 are interposed between the skin member 103C and the pad 103B in that order, but may also be reversed in order, by placing the pressure sensor sheet 114 on top of the soft actuator sheet 118. In the latter case, the sensitivity of the pressure sensor sheet 114 can be improved.

In the foregoing embodiments, the channels 132 for receiving the wires 120 and 122 are defined by the grooves 130 formed in the sub frame 103A and the recesses 131 formed in the pad member 103B, but only the grooves 130 or the recesses 131 may be formed in the corresponding depending on the diameters of the wires 120 and 122.

Figure 17:
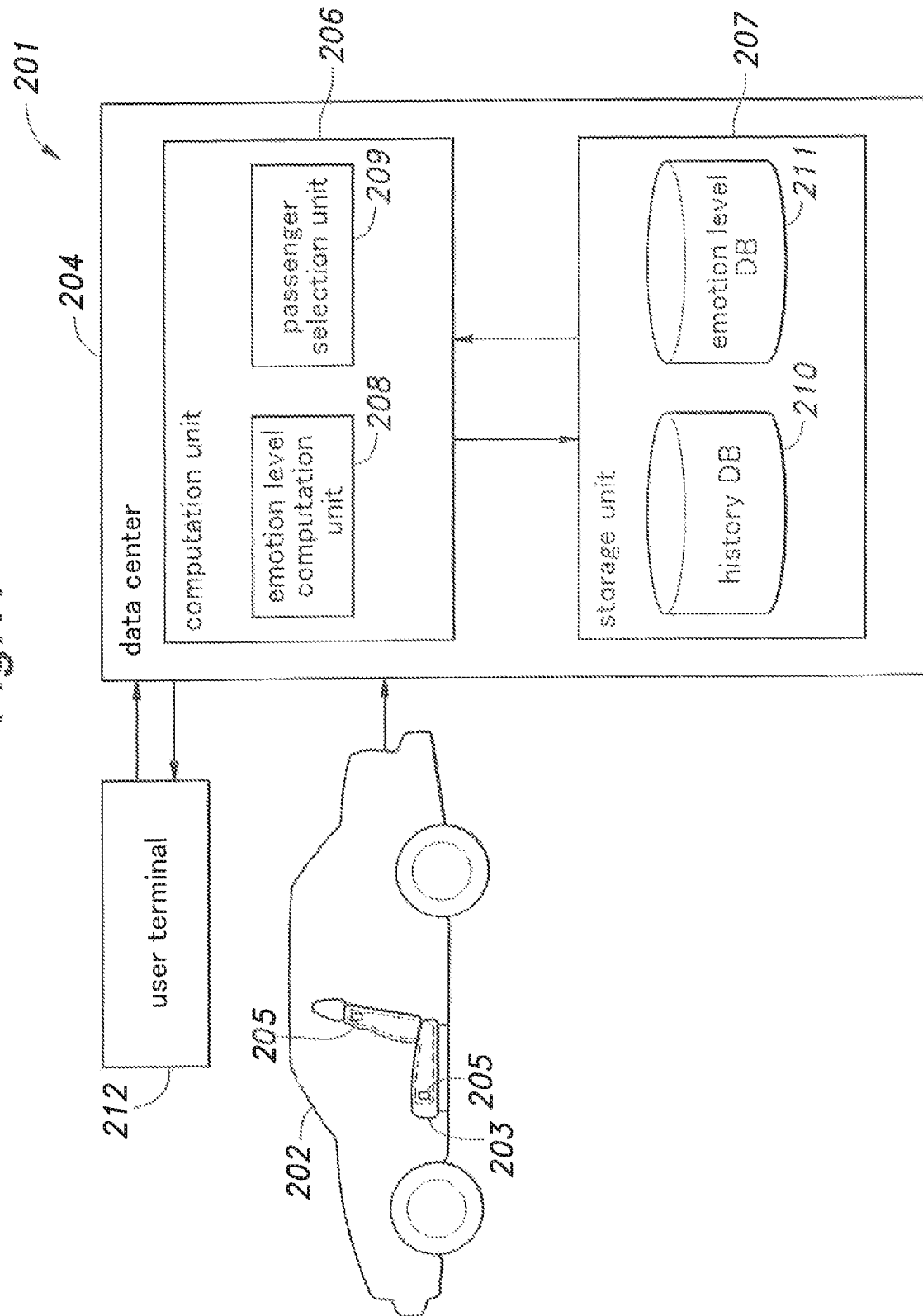
FIG. 17 is a block diagram of a passenger selection system according to an embodiment of the present invention.

FIGS. 17 and 18 show a third embodiment of the present invention. A ride sharing system 201 for a vehicle 202 includes a detection unit 205 provided on the seat 203 (a seat cushion and a seat back of the seat 203, respectively) and a data center 204 provided separately from the vehicle 202 typically at a fixed location. The detection unit 205 in this case essentially consists of a biometric sensor 205.

The biometric sensor 205 is configured to detect indices relating to human emotion. The detection values of the indices detected by the biometric sensor 205 are forwarded to the data center 204 via a wireless communication between a transmitter provided on the vehicle 202 and a receiver provided on the data center 204. The biometric sensor 205 detects indices for each of the occupants of the vehicle 202. For example, the biometric sensor 205 may consist of a device for measuring the pulses, body temperature, brain waves and the like of an occupant of the seat 203, a device for detecting liquid or gas secreted from the skin of an occupant such as perspiration and gases, and/or a device for measuring the electric conductance of the skin that can be changed by perspiration or the like. Other sensors may also be used as the biometric sensor 205. The biometric sensor 205 may be fixedly attached to the seat 203 or the like of the vehicle 202 or may be portable like a wristband or the like that may be worn by the occupant. The biometric sensor 205 may be kept in contact with the occupant or may be positioned remotely from the occupant.

When the biometric sensor 205 is fixedly attached to the seat 203, there is no need for the user to wear the biometric sensor 205, and since the biometric sensor 205 is positioned close to the seated occupant, gas or the like secreted from the occupant's skin can be detected in a reliable manner. When the biometric sensor 205 is provided in the wristband, the biometric sensor 205 can be brought into contact with the skin of the occupant so that the detection or measurement of the pulse rate, body temperature, perspiration, and/or skin electrical resistance of the occupant can be facilitated. The biometric sensor 205 may consist of a single sensor, but may also consist of two or more biometric sensors in order to detect indices relating to two or more kinds of emotions of the occupant in order to improve the accuracy of obtained information. It is preferable that the detection values of the indices detected by the biometric sensor 205 be transmitted to the data center 204 by wireless transmission so that the emotion data can be transmitted from the biometric sensor 205 to the data center 204 both easily and quickly.

The data center 204 includes an information processing device such as a personal computer including a computation unit 206 and a storage unit 207. The data center 204 is preferably provided separately or independently from the vehicle 202 so that the data may be centrally managed, and the risk of leakage of personal information may be minimized. The computation unit 206 includes an emotion level computation unit 208 that computes an emotion level (which may be favorable in one extreme and unfavorable in the other extreme) of each occupant toward each of the other occupants according to the values of the indices detected by the biometric sensor 205, and a passenger selection unit 209 for selecting a combination of passengers based on the emotion levels. The storage unit 207 functions as an emotion history database 210 that stores the detected values of the indices detected by the biometric sensor 205 as data representing the emotion level of each passenger toward each of the passengers sharing the ride with the passenger in question in each instance of ride share, and an emotion level database 211 for storing the emotion levels computed and analyzed by the emotion level computation unit 208.

Each user of the system 201 is provided with a user terminal 212 such as a smart phone and a personal computer that can communicate with the data center 204. The user terminal 212 transmits the time, the start point and the destination, along with a user ID, entered by the user to the data center 204, and receives a determined combination of passengers from the data center 204.

The process of determining a combination of passengers for sharing a ride is described in the following with reference to the flowchart shown in FIG. 18. Each user of the system 201 performs a user registration, and acquires a user ID.

The data center 204 receives a user ID, and the time, the start point and the destination for a planned trip from each user terminal 212 (step ST1).

The passenger selection unit 209 analyzes the time, the start point and the destination entered by each user, and determines a route for the vehicle, and a combination of candidate passengers who are going to share a ride with each of a plurality of vehicles (step ST2).

The passenger selection unit 209 then selects the fellow passengers for each user based on the history of emotion levels of the user stored in the emotion level database 211 (step ST3). Once the user begins the ride as specified by the data center 204, the biometric sensor 205 starts measuring the emotion level of each of the passengers of the vehicle (step ST4). The measured emotion levels are transmitted to the data center 204 (step ST5). The data center 204 stores the received data in the history database 210, and analyzes the received data. The analysis results are stored in the emotion level DB 211. At the same time, the old data is discarded according to a predetermined rule (step ST7).

In this embodiment, the higher an emotional level value is, the more favorable the emotion of the user toward a potential fellow passenger is. The passenger selection unit 209 may select a combination of passengers for sharing a ride in such a way that the average of the emotional level values of the combination of the passengers may be maximized.

For instance, suppose that there are six users who desire to share a ride by using two vehicles, and each vehicle is to be assigned to three of the entire users. In such an instance, each user demonstrates a certain emotion level in relation to the two fellow passengers during the shared ride. It is therefore impossible to determine how the emotional level of the user may be attributed to each of the fellow passengers from a single instance of a ride share. Therefore, by accumulating the history of emotion levels of each user toward the other users over the past ride share instances, it is possible to discern the emotion level of the user toward each of the remaining users.

Thus, in this case, the data center 204 is able to determine the emotion levels of each user toward the remaining five users, and determine the two fellow passengers who give rise to high emotional level values.

In this case, each vehicle gives rise to six emotional level values. In order to optimize the entire emotional levels, the three passengers for each vehicle may be selected such that the average of the six emotional level values is maximized. Preferably, the selection may also be made so that the average of the six emotional level values for one vehicle is not much different from that of the other vehicle.

Alternatively, the passenger selection unit 209 may select a combination of passengers for sharing a ride in such a way that the average of the emotional level values of one of the passengers is maximized. This particular passenger may be the one who is going to drive the vehicle, or the one who pays an extra charge.

Also, the passenger selection unit 209 may select a combination of passengers for sharing a ride in such a way that a worst combination of passengers may be avoided.

For instance, the passenger selection unit 209 selects the passengers of the vehicles in the order of receiving requests for sharing a ride. Once a vehicle is filled, any additional user requesting a ride is assigned to a next vehicle. During this process, if there is any combination of two passengers which gives rise to an emotion level value lower than a prescribed value, the passenger selection unit 209 avoids this particular combination by moving one of the passengers to another vehicle. Thereby, a discomfort owing to an undesirable combination of passengers can be avoided.

In an alternate embodiment, the passenger selection unit 209 groups users into a plurality of groups in such a manner that any two users in a same group give rise to favorable emotion level values. When selecting the combination of each vehicle, the passenger selection unit 209 selects the combination of passengers for each vehicle so that passengers belonging to a same group may be preferentially assigned to a same vehicle.

The users then share rides with other users. The biometric sensor 205 on each vehicle detects the indices representing the emotion of each passenger, and the data obtained by the biometric sensor 205 is transmitted to the data center 204. The data is associated with the user ID of each user, and the user ID of each fellow passenger. The obtained data is stored in the emotion history database 210 (step ST6). New data is added to the existing data each time the subject user shares a ride with other users. In this embodiment, a limit is set on the amount of data stored for each user, and the oldest part of the data may be discarded as new data is obtained (or, in other words, the emotion history is updated each time the user shares a rider with other users) (step ST7).

The current emotion levels of one user toward other users can be computed from the past history of the particular user toward the respective other users. The emotion level may be evaluated based on a single index or a plurality of indices. If only one index is used as the emotion level data, the emotional level data may be simply evaluated as an average value. If two or more indices are used as the emotion level data, a weighted average may be used as the emotional level data.

If desired, the emotion level data may be based on an emotion of a subject user toward a combination of two or more users.

When a user shares a ride with a new user with whom the subject user has never shared a ride, the emotion level toward the new user may be set to a freely selected initial value (a typical value, for instance). Alternatively, an emotion level of a subject user toward a new user may be based on the emotion level of another user toward the new user. The present application is applicable not only to automobiles but also to other modes of transportation such as buses, ships and aircraft.

The invention claimed is:

1. A vehicle seat, comprising:
   a frame member provided on a floor of a vehicle, the frame member including a lower frame part extending in a fore and aft direction and an upper frame part extending substantially upward from a rear end of the lower frame part;
   a plurality of seat parts detachably attached to the frame member, the seat parts including a seat cushion, a seat back, and a head rest;
   a mechanical connector device provided on the lower frame part, the upper frame part, and each of the seat parts for detachably attaching each of the seat parts to the frame member; and
   an electric connector device provided on the lower frame part, the upper frame part, and each of the seat parts for electrically connecting an electric component provided on each of the seat parts to an electric component provided on the frame member;
   wherein the electric connector device is integrally incorporated in the mechanical connector device;
   the lower frame part and the upper frame part are each made of a hollow tubular member defining an inner space, and
   the inner space receives the electric component.

2. The vehicle seat according to claim 1, wherein the mechanical connector device is provided with a first tube provided on the seat parts and a second tube provided on the frame member and configured to be fitted into or onto the first tube, and the electric connector device includes a first part received in the first tube and a second part received in the second tube.

3. The vehicle seat according to claim 2, wherein the first part of the electric connector device is provided with an identifier carrying prescribed information, and the second part of the electric connector device is provided with a recognition device configured to read information carried by the identifier.

4. The vehicle seat according to claim 1, wherein the inner space of the upper frame part receives an air bag device; and
   the electric component includes the control device received in the inner space and electrically connected to the air bag device via wires passed through the inner space.

5. The vehicle seat according to claim 4, wherein the lower frame part is attached to the floor via a plurality of legs, the control device is connected to an onboard power source via a power cable, and the power cable extends to the power source via the inner space and the interior of one of the legs.

* * * * *